(12) United States Patent
Mathison et al.

(10) Patent No.: US 6,586,403 B1
(45) Date of Patent: Jul. 1, 2003

(54) TREATING ALLERGIC REACTIONS AND INFLAMMATORY RESPONSES WITH TRI- AND DIPEPTIDES

(75) Inventors: Ronald Mathison, Calgary (CA); Essam Metwally, Calgary (CA)

(73) Assignee: Salpep Biotechnology, Inc., Calgary (CA)

( * ) Notice: Subject to any disclaimer, the term of this patent is extended or adjusted under 35 U.S.C. 154(b) by 62 days.

(21) Appl. No.: 09/620,249

(22) Filed: Jul. 20, 2000

(51) Int. Cl.$^7$ .................. A61K 38/05; A61K 38/06; C07K 5/06; C07K 5/08

(52) U.S. Cl. .................. 514/18; 514/19; 530/331; 548/496; 562/448; 562/450; 562/561

(58) Field of Search .................. 514/18, 19; 530/331; 562/448, 450, 507, 561; 548/496

(56) References Cited

U.S. PATENT DOCUMENTS

| | | | |
|---|---|---|---|
| 4,880,779 A | 11/1989 | Gallaher | 514/15 |
| 6,117,840 A | * 9/2000 | Arrhenius et al. | 514/19 |

FOREIGN PATENT DOCUMENTS

| | | |
|---|---|---|
| WO | WO-98/06742 A2 | * 2/1998 |

OTHER PUBLICATIONS

Llinas–Brunet et al. Phosphotyrosine–Containing Dipeptides as High–Affinity Ligands for the p56lck SH2 Domain. J. Med. Chem. 1999, vol. 42, No. 4, pp. 722–729.*

Mathison et al., "Removal of the Submandibular Glands Increases the Acute Hypotensive Response to Endotoxin," *Circulatory Shock*, 1993, pp. 52–58, vol. 39, Wiley–Liss, Inc., New York, New York.

Mathison et al., "Neuroendocrine Regulation of Inflammation and Tissue Repair by Submandibular Gland Factors," *Immunology Today*, 1994, pp. 527–32, vol. 15, No. 11, Elsevier Science, Ltd., New York, New York.

Mathison, "The Submandibular Glands: a role in homeostasis and allostasis," *Biomedical Reviews*, 1995, pp. 61–69, vol. 4, Highwire Press, New York, New York.

Mathison et al., "A Novel Submandibular Gland Peptide Protects Against Endotoxic and Anaphylactic Shock," *Am. J. Physiol.*, 1997, pp. R1017–R1023, vol. 273, The American Physiological Society, Bethesda, Maryland.

(List continued on next page.)

*Primary Examiner*—Jeffrey E. Russel
(74) *Attorney, Agent, or Firm*—Burns, Doane, Swecker & Mathis, L.L.P.

(57) ABSTRACT

This invention relates to methods and compositions of tripeptides and dipeptides having anti-inflammatory activities that can be used for the treatment of allergic and inflammatory reactions. A peptide of the formula:

$$X-R_1-R_2-R_3-Y \quad (I)$$

or $$X-R_1-R_2-Y \quad (II)$$

wherein X is selected from the group consisting of H and acetyl; $R_1$ is selected from the group consisting of D or L-phenylalanine; tyrosine; tryptophan; phenylglycine; Nor-methylphenylalanine; cyclohexylalanine; and norleucine; $R_2$ is selected from the group consisting of D or L-glutamate; and aspartate; and in the case of peptide (II), $R_3$ is selected from the group consisting of glycine; D or L-alanine; beta-alanine; valine; leucine; isoleucine; sarcosine; and gamma-aminobutyric acid or another aliphatic amino acid; and Y is selected from the group consisting of OH and $NH_2$, but excluding the dipeptides H-L-Phe-L-Glu-OH, H-L-Trp-L-Glu-OH, H-D-Phe-D-Glu-OH and H-D-Trp-D-Glu-OH.

32 Claims, 14 Drawing Sheets

Dose-dependent inhibition by feG and feG(NH2) of intestinal motility disturbances caused by intravenous endotoxin. The results are presented as the mean ± SEM. Number of animals = 8 to 10. Significance: *P<0.05; *P<0.01 when compared to saline treated control.

OTHER PUBLICATIONS

Mathison et al., "Submandibular Gland Peptide–T (SGP–T) Inhibits Intestinal Anaphylaxis," *Digestive Diseases and Sciences*, 1997, pp. 2378–2383, vol. 42, No. 11, Wolters Kluwer, Amsterdam, The Netherlands.

Mathison, "Reduction in cardiovascular anaphylaxis by submandibular gland peptide–T," *Proc. West. Pharmacol. Soc.,* 1997, pp. 73–74, vol. 40.

Mathison et al., Attenuation of Intestinal and Cardiovascular Anaphylaxis by the Salivary Gland Tripeptide FEG and Its D–Isomeric Analog feG, *Peptides*, 1998, pp. 1037–1042, vol. 19, No. 6, Elsevier Science, New York, New York.

Nkemdirim et al., "Modulation of neutrophil activity by submandibular gland peptide–T (SGP–T)," *Polish Journal of Pharmacology*, 1998, pp. 417–24, vol. 50, Polish Academy of Sciences, Cracow, Poland.

Ramaswamy et al., "Marked Antiinflammatory Effects of Decentralization of the Superior Cervical Ganglia," *Journal of Exp. Med.,* 1990, pp. 1819–1830, vol. 172, The Rockefeller University Press, New York, New York.

Schullek et al., "A High–Density Screening Format for Encoded Combinatorial Libraries: Assay Miniaturization and Its Application to Enzymatic Reactions," *Anal. Biochem.,* 1997, pp. 20–29, vol. 246, Academic Press, New York.

Dery, Rene E., "Inhibition of airway inflammation by feG: A C–terminal Peptide isolated from rat sumandibular gland prohormone SMR1", 1999 Alberta Respiratory Disease Symposium, Oct. 22–24, 1999.

Mathison, R., et al., "Regulation of Neutrophil Function by SMR1 C–Terminal Peptides", Shock 13 (Suppl):52, 2000.

Turesin, F., et al., "The Role of Submandibular Gland Peptide feG in Anaphylaxis–Induced Cardiac Inflammation", Shock 13 (Suppl):52, 2000.

Befus, D., et al., "C–Terminal Peptides of the Prohormone SMR1 Inhibit Allergic Inflammation in the Airways", CSI2000, Mar. 17/20, 2000, Quebec, Canada.

Dery, Rene E., et al., "A Novel Peptides Isolated from Prohormone SMR1 Inhibits Allergic Inflammation of the Airways", ATS 2000, May 5–10, 2000, Toronto, Canada.

Befus, Dean, et al., "Inhibition of Allergic Inflammation by C–Terminal Peptides of SMR1", CIA May 18/24, 2000, Japan.

Mathison, R., et al., "Reduction of endotoxin–induced leukocyte activation in the rat intestine by a D–isomeric analogue of salivary gland tripeptide FEG", American Gastroenterology Association, Digestive Diseases Week, San Diego, California, May 21–24, 2000.

Befus, D., et al., "Cervical Sympathetic Nerve Trunk–Submandibular Gland Axis: Neural Control of Anti–inflammatory Peptides that Modulate Airways Inflammation", Canib Symposium, Jun. 9–12, 2000, Winnipeg, Canada.

Davison, J.S., et al., "Salivary Gland Peptides: Their Role in Anaphylaxis and LPS–Induced Inflammation", Canib Symposium (Not dated).

Mathison, R., et al., "The D–isomeric Analog of Salivary Glant Tripeptide FEG Reduces Endotoxin Induced Cell Activation in the Rat Intestine", Falk Symposium: Neuro-gastro-enterology—From the Basics to the Clinics, Jun. 21/22, 1999.

Munch, G., et al., "Amino acid specificity of glycation and protein—AGE crosslinking reactivities determined with a dipeptide SPOT library", Nature Biotechnology, vol. 17, Oct. 1999, 1006–1010.

Hwang, S., et al., "Inhibition of gene expression in human cells through small molecule–RNA interactions", PNAS: Nov. 9, 1999, vol. 96, No. 23, 12997–12998.

Schullek, J., et al., "A High–Density Screening Format for Encoed Combinatorial Libraries: Assay Miniaturization and its Application to Enzymatic Reactions", Analytical Biochemistry 246, 20–29 (1997).

Slootstra, J.W., et al., "Structural aspects of antibody–antigen interaction revealed through small random peptide libraries", Molecular Diversity, 1 (1996) 87–96.

R.D. Mathison, et al., "Reduction in Cardiovascular Anaphylaxis by Submandibular Gland Peptide–T", Proc. West. Pharmacol. Soc. 40: 73–74 (1997).

R.D. Mathison, et al., "Inhibition of Leukocyte Rolling by Submandibular Gland Peptide–T (SGP–T)", Proc. West. Pharmacol. Soc. 42:39–40 (1999).

R. Mathison, et al., "Attenuation of Intestinal and Cardiovascular Anaphylaxis by the Salivary Gland Tripeptide FEG and its D–isomeric Analog feG", Peptides, vol. 19, vol. 6, 1037–1042, 1998.

R. Mathison, et al., "Submandibular Gland Peptide–T (SGP–T) Inhibits Intestinal Anaphylaxis", Digestive Diseases and Sciences, vol. 42, No. 11 (Nov. 1997).

R. Mathison, et al., "Submandibular Gland Peptide–T (SGP–T): Modulation of Endotoxic and Anaphylactic Shock", Drug Development Research 42:164–171 (1997).

R. Mathison, et al., "A novel submandibular gland peptide protects against endotoxic and anaphylactic shock", American Physiological Society, 273:R1017–R1023, 1997b.

* cited by examiner

FIGURE 1

Effects of C-terminus substitutions, N-terminus substitutions, aromatic substitution at position 1, and Asp substitution at position 2 in both L and D forms in FEG, and removal of the glycine on inhibition of intestinal anaphylaxis *in vitro*.

| Abbreviation | Structure[a] | OA/Ure[b] | % Control | n[c] |
|---|---|---|---|---|
| Control | Saline | 0.27 ± 0.02 | 100 | 41 |
| FEG | FEG | 0.12 ± 0.04 * | 47 | 4 |
| AEG | [$A_1$]FEG | 0.25 ± 0.11 | 93 | 4 |
| GEG | [$G_1$]FEG | 0.20 ± 0.08 | 74 | 6 |
| Ac-FEG | Acetyl-FEG | 0.17 ± 0.05 | 63 | 5 |
| FEG-NH$_2$ | FEG-NH$_2$ | 0.26 ± 0.08 | 96 | 4 |
| FEβAla | [βAla$_3$]FEG | 0.09 ± 0.01 | 33 | 4 |
| FESar | [Sarcosine$_3$]FEG | 0.16 ± 0.03 | 59 | 4 |
| feG | [$f_1e_2$]FEG | 0.14 ± 0.03 * | 52 | 4 |
| FDG | [$D_2$]FEG | 0.26 ± 0.04 | 98 | 4 |
| fdG | [$f_1d_2$]FEG | 0.40 ± 0.12 | 148 | 7 |
| WEG | [$W_1$]FEG | 0.13 ± 0.05 * | 48 | 5 |
| weG | [$w_1e_2$]FEG | 0.20 ± 0.05 | 75 | 4 |
| WDG | [$W_1D_2$]FEG | 0.12 ± 0.03 * | 46 | 10 |
| wdG | [$w_1d_2$]FEG | 0.20 ± 0.04 | 75 | 7 |
| YEG | [$Y_1$]FEG | 0.31 ± 0.03 | 115 | 4 |
| yeG | [$y_1e_2$]FEG | 0.13 ± 0.03 * | 50 | 4 |
| YDG | [$Y_1D_2$]FEG | 0.22 ± 0.11 | 83 | 3 |
| ydG | [$y_1d_2$]FEG | 0.21 ± 0.08 | 78 | 3 |
| (Phg)EG | [Phg$_1$]FEG | 0.15 ± 0.05 * | 59 | 6 |
| (NMeF)EG | [NMeF$_1$]FEG | 0.13 ± 0.05 * | 49 | 8 |
| (Cha)EG | [Cha$_1$]FEG | 0.09 ± 0.04 * | 34 | 6 |
| (Nle)EG | [Nle]FEG | 0.17 ± 0.05 * | 64 | 7 |
| IEG | [$I_1$]FEG | 0.22 ± 0.03 | 82 | 7 |
| LEG | [$L_1$]FEG | 0.20 ± 0.05 | 75 | 10 |
| (Nval)EG | [NVal$_1$]FEG | 0.25 ± 0.04 | 94 | 6 |
| FE | FE | 0.18 ± 0.02 | 67 | 19 |
| fe | [$f_1e_2$]FE | 0.16 ± 0.01 * | 59 | 8 |
| (cha)e | [cha$_1e_2$]FEG | 0.19 ± 0.02 * | 70 | 9 |

[a] All peptides have the general structure $X-R_1-R_2-R_3-Y$. The nomenclature designated $[f_1e_2]FEG$ reads as follows: $f_1$ = D-phenylalanine in position 1 replaces L-phenylalanine (F) in position 1; $e_2$ = D-glutamate in position 2 replaces L-glutamate (E) in position 1 and the glycine (G) is unchanged. Similarly, $[D_2]FEG$ reads $D_2$ = D-aspartate in position 2 replaces L-glutamate (E) in position 2 and the glycine (G) is unchanged, and the phenylalanine (F) and glycine remained unchanged.

[b] OA/URE: Contractile response to ovalbumin (OA) divided by contractile response to Urecholine (URE)

[c] n: Number of tissues

FIGURE 2. The tripeptide YEG is an antagonist of the inhibitory actions of the general formula A peptide of the formula (I) XEG; X is an aromatic amino acid such as D-phenylalanine (feG) or L-Nor-methylphenylalanine (NMeF)EG, but is not an aliphatic amino acid such as L-Cyclohexylalanine or L-Norleucine. The results are presented as the mean ± SEM. The number of animals is from 6 to 8. Significance: * $P<0.05$; *$P<0.02$.

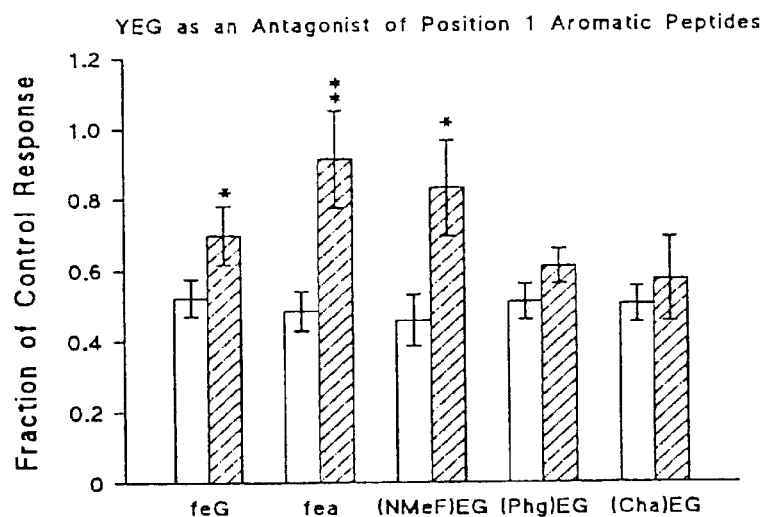

FIGURE 3a. Inhibition by SGP-T, feG and feG(NH2) of intestinal motility disturbances caused by intravenous endotoxin. The results are presented as the mean ± SEM. Number of animals = 3 to 15. Significance: *P<0.05; *P<0.01 when compared to saline treated control.
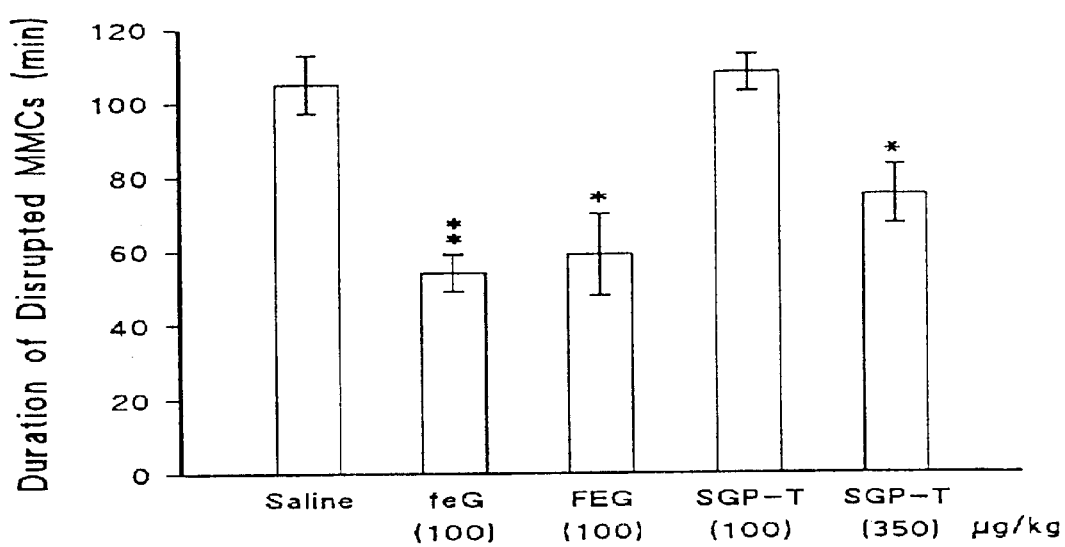

FIGURE 3b. Dose-dependent inhibition by feG and feG(NH2) of intestinal motility disturbances caused by intravenous endotoxin. The results are presented as the mean ± SEM. Number of animals = 8 to 10. Significance: *P<0.05; *P<0.01 when compared to saline treated control.
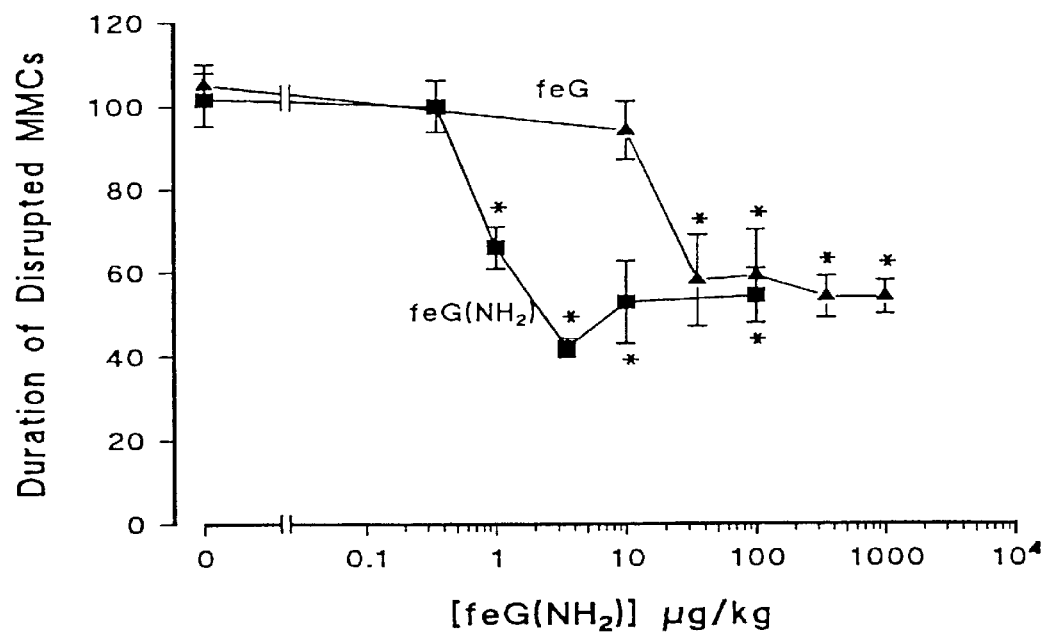

FIGURE 4. Inhibition by feG of leukocyte accumulation in peritoneal lavage fluid following intraperitoneal injection of lipopolysaccharide (LPS). Total and differential cell counts in peritoneal lavage of rats receiving intraperitoneal administration of lipopolysaccharide (LPS; 2 mg/kg ip (A) or 20μg/kg iv (B)) with and without intraperitoneal treatment with feG (100 μg/kg). Levels of significance: * greater than saline $P<0.05$; # less than LPS $P<0.05$; n = 4 to 6.

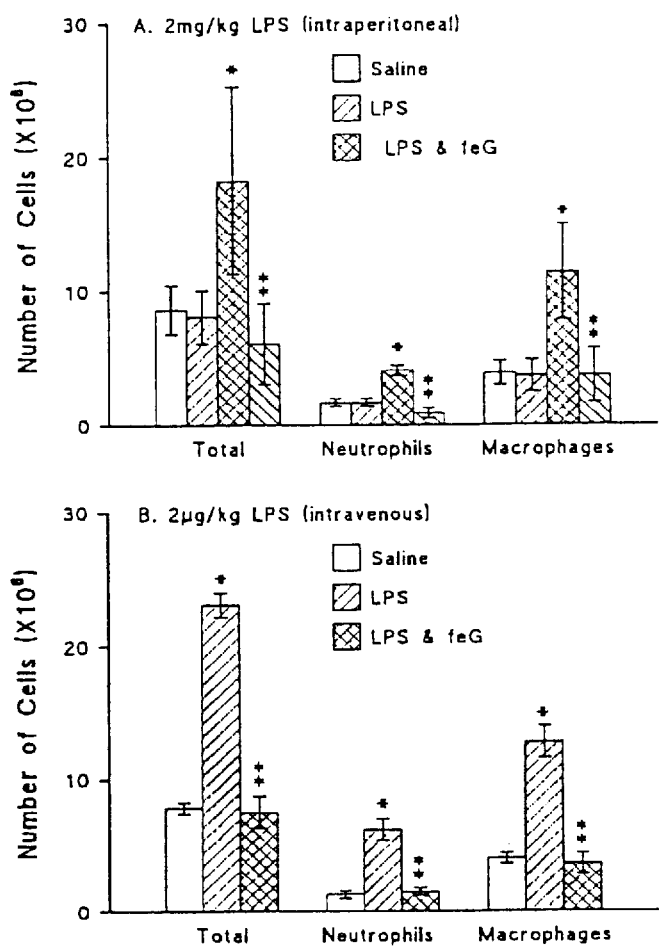

FIGURE 5. Inhibition by feG of leukocyte accumulation (ED9 marker) and activation (CD18 marker) in the jejunal smooth muscle of rats following intraperitoneal injection of lipopolysaccharide (LPS). Number of positive interstitial cells in the muscle layers of the jejunum of rats receiving either 2 mg/kg of LPS intraperitoneally (A) or 20 µg/kg of LPS intravenously (B) with and without intraperitoneal treatment with feG (100 µg/kg). Number of cells per 40X field. Significance: *$P<0.05$ greater than saline; #$P<0.05$ less than LPS; n = 4 to 6.

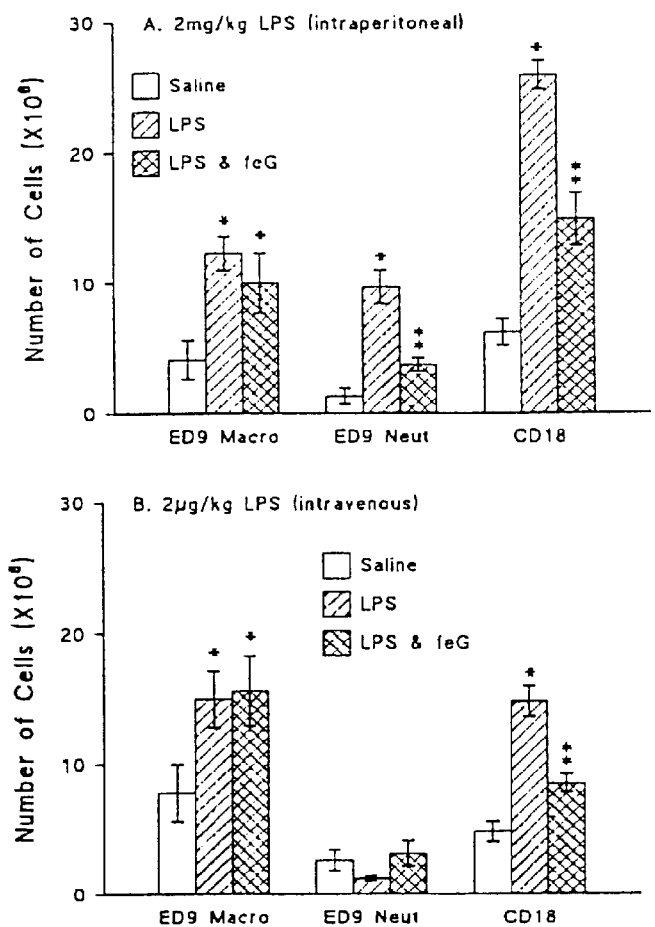

FIGURE 6. The tripeptide feG inhibits the histamine induced wheal response in the skin. The results are presented as the mean ± SEM. Number of animals = 8 to 10. Significance: *P<0.05; *P<0.01 when compared to saline treated control.
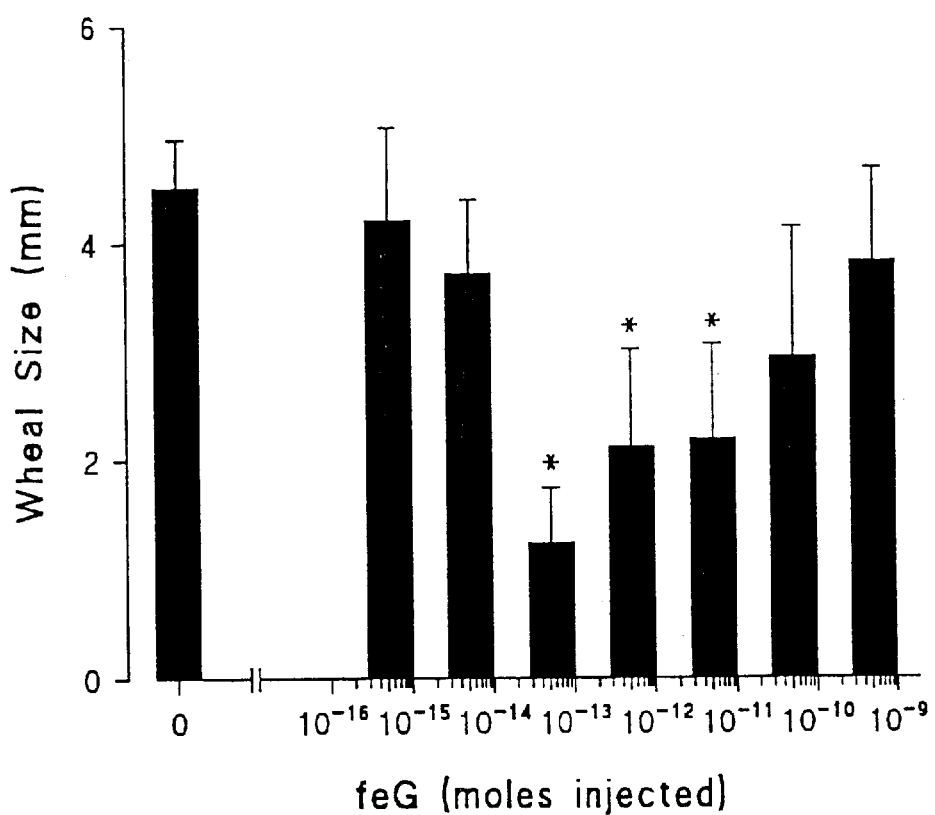

FIGURE 7. Effects of feG on the binding of leukocytes to atrial slices.

| Treatment | No PAF | PAF |
|---|---|---|
| Saline | 6.2±1.0 (14)† | 12.2±2.2* (10) |
| feG ($10^{-9}$M) | 7.5±1.6 (14) | 5.2±0.8 (9)# |

The results are presented as the mean ± SEM. † number of experiments in parenthesis.

Significance: $P< 0.05$ for * greater than Saline and No PAF; # less than Saline and PAF FIGURE 8. Time course of the oral feG administration on pulmonary inflammation occurring 24 h after exposure to aerosolized 5% ovalbumin.
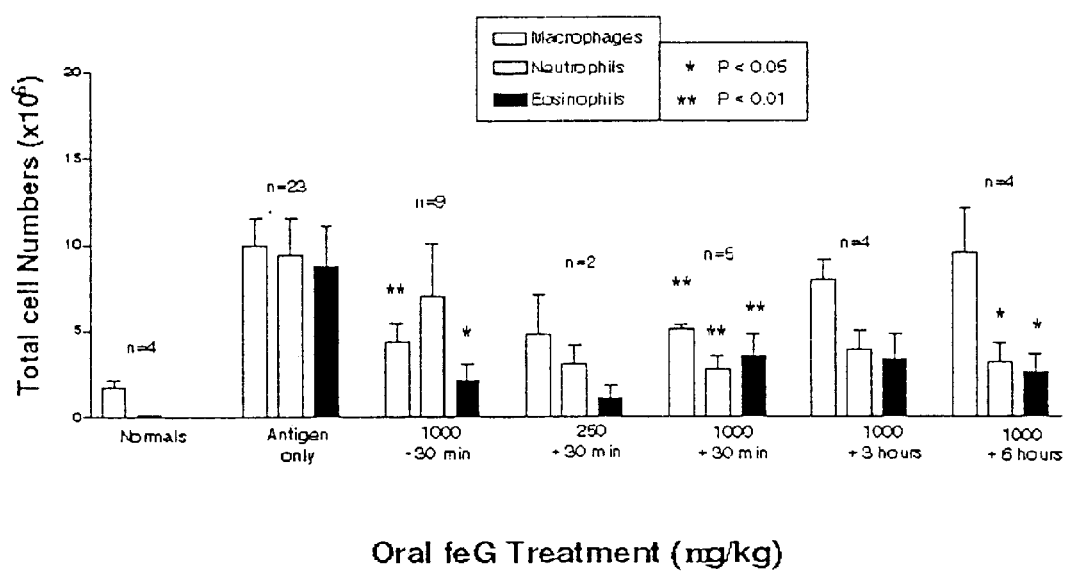

Figure 9. Inhibitory effect of feG on allergen induced hyperresponsiveness to methacholine. feG as administered at a dose of 1 mg/kg orally. *P<0.05 by ANOVA.
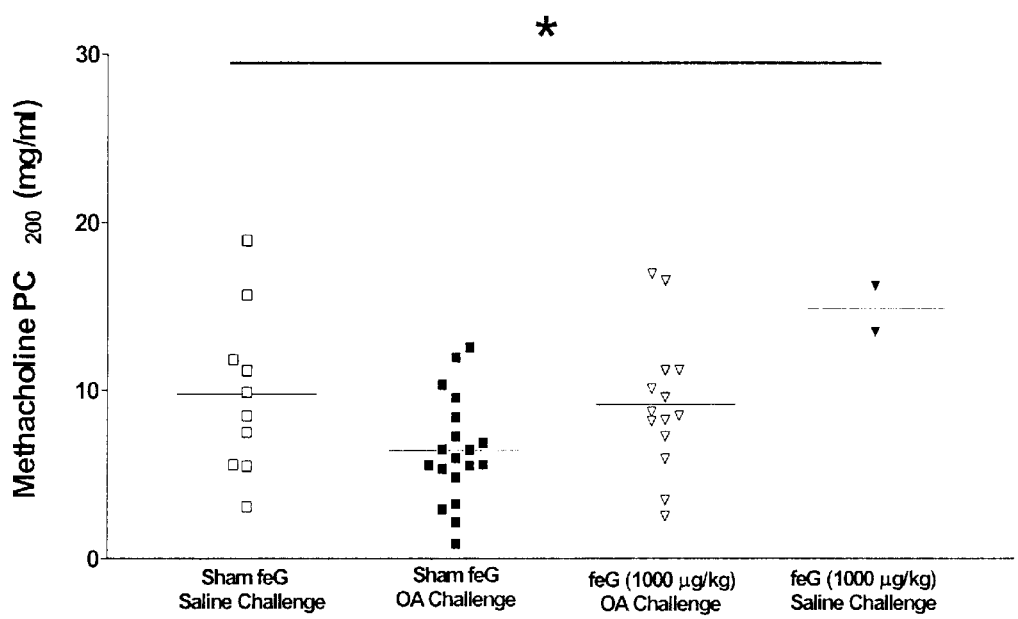

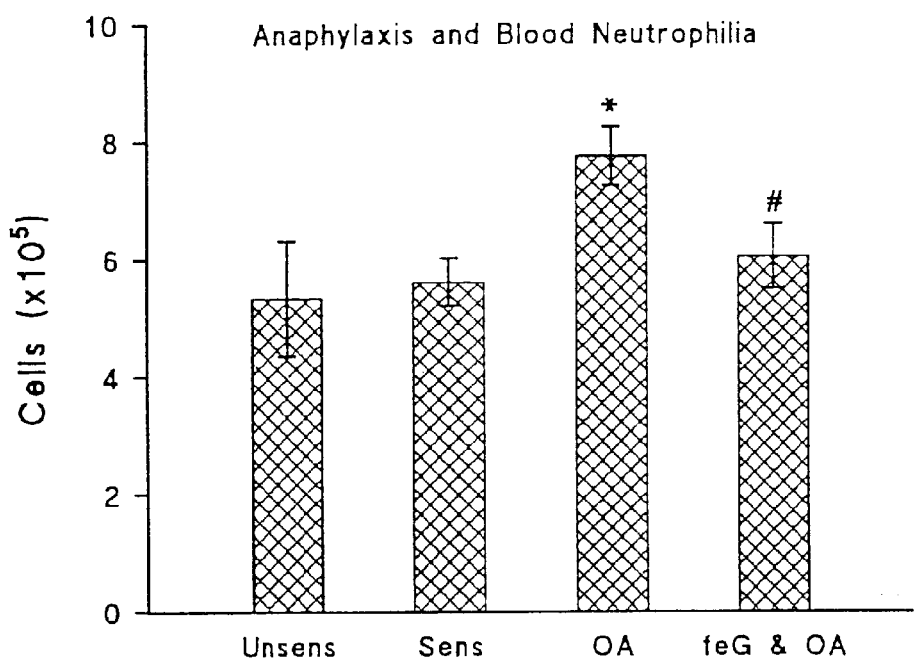
FIGURE 10. Prevention by feG of the blood neutrophilia caused by an anaphylactic reaction in Hooded-Lister rats. The results are presented as the mean ± SEM. Number of animals = 3 to 7. Significance: *$P<0.05$.

FIGURE 11. Inhibition of the platelet activating factor (PAF) induced expression of CD11b and CD16b expression on human neutrophils by di- and tripeptides. Data represents mean ± SEM for number of experiments shown in parenthesis. Significance: * P<0.05.

Inhibition of PAF Induced Upregulation of CD11b and CD16b

| Peptide | CD11b | CD16b | CD16b |
|---|---|---|---|
|  |  | 1±30 |  |
| SGP-T |  | -56±49; (11) | -35±16; (3) |
| FeG | -77±26; (8)* | -84±27; (11)* | -96±27; (8)* |
| FEG | -5±18; (5) | -157±69; (7)* | -32±44; (5) |
| FEA | -4±27; (6) | -255±94; (7)* | -27±17; (5) |
| Fea | -67±37; (6)* | -73±19; (7)* | -2±7; (4) |
| FeA | 3±25; (7) | -149±52; (7)* | -63±31; (5)* |
| Fea | -11±33; (6) | -73±59; (7) | -34±17; (6) |
| YeG | -82±22; (12)* | -42±28; (6) | -28±33; (12) |
| YEG | -10±15; | -13±47; (7) | +17±54; |
| (Phg)EG | -38±23; (4) | -82±62; (6) | -92±19; (4)* |
| (NMeF)EG | +3±27; (5) | -62±45; (7) | -116±56; (5)* |
| FEG(NH2) | 16±43; (5) | -51±53; (7) | -42±21; (5) |
| Ac-FEG | -15±40; (5) | -99±65; (7) | -26±38; (5) |
|  |  |  |  |
| (Nle)EG | 1±35; (3) | -77±35; (7)* | +3±47; (3) |
| (Cha)EG | 22±28; (5) | -188±61; (7)* | -7±28; (5) |
| FeG(NH2) | 8±35; (5) | -198±91; (7)* | -38±36; (5) |
| fe | 59±25; (4) | -157±65; (7)* | -77±41; (5)* |
| (cha)e(NH2) | -2±32; (5) | -157±57; (4)* | -72±36; (5) |
| FE | -5±18; (5) | -91±78; (5) | -60±40; (5) |
| (cha)e | +41±22; (4) | -23±50; (5) | -162±97; (5)* |
| ye | -2±26; (4) | -23±21; (5) | -31±50; |
| ye(NH2) | +25±4; (4) | -89±90; (5) | +19±16 |

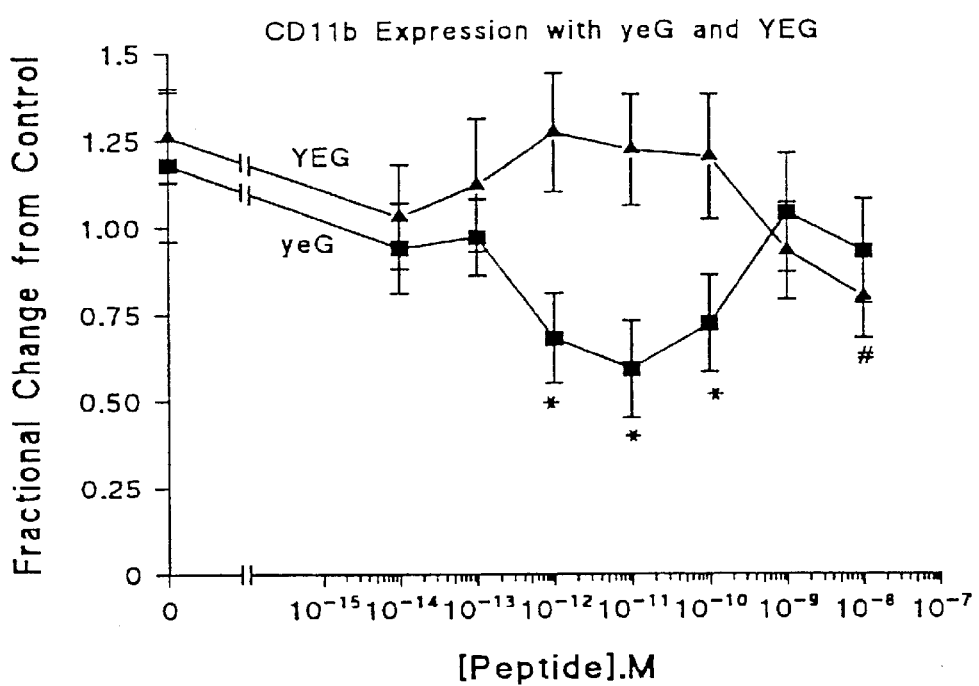
FIGURE 12. Inhibition by yeG of platelet activating factor (PAF) induced expression of CD11b on human neutrophils. Data represents mean ± SEM of 7 experiments for yeG and 3 experiments for YEG. Significance: * $P<0.05$ for yeG; # $P<0.05$ for YEG.

TREATING ALLERGIC REACTIONS AND INFLAMMATORY RESPONSES WITH TRI- AND DIPEPTIDES

FIELD OF THE INVENTION

The present invention relates to peptides having anti-inflammatory properties. In particular, the present invention relates to peptides through actions on cells that modify the leukocyte recruitment and activation cascade and the actions of mediators released from inflammatory cells on target cells and tissues, including smooth muscle of animals, as well as humans.

BACKGROUND OF THE INVENTION

Immediate or Type 1 allergic reactions are largely attributed to IgE antibodies, although IgG antibodies can participate in and modulate allergic reactions. The allergy is generally caused by the activation of a subpopulation of immune cells, the mast cells and basophils. When antigen reacts with IgE antibody receptors on the cell's surface the chemical mediators initiate the allergic reaction by acting on adjacent immune, epithelial, endothelial and smooth muscle cells and promote, in a longer term, the influx of other inflammatory and immune cells (neutrophils, eosinophils, monocytes, lymphocytes) into tissue. This influx of inflammatory cells predisposes the patient to recurrent and sometimes delayed, or prolonged allergic or hypersensitivity reactions. A distinction between immediate and delayed allergic reactions and delayed, chronic immune injury can also be made. The Type 1 allergic reactions are defined according to the location where they occur. Asthmatic reactions occur in the lungs, rhinitis in the nose, conjunctivitis in the eyes, and atopic dermatitis in the skin, systemic allergic reactions in the circulation and intestinal reactions in the gastrointestinal system.

Asthma can be defined clinically as a condition of intermittent, reversible airways obstruction, and manifests itself as several clinical entities: allergic asthma, bronchial asthma, exercise induced asthma (EIA), chemical induced asthma, and status asthmaticus Asthma can be divided into two types. Extrinsic asthma is generally triggered by external agent such as allergens (dust mites, pollen, stings, drugs, or foods), and is commonly diagnosed in early life. Intrinsic asthma, which generally develops later in life, can be triggered by congested and inflamed tissues, infection, endogenous catecholamines (e.g. adrenaline), drugs (e.g. aspirin), stress or exertion.

Rhinitis, allergic conjunctivitis and atopic dermatitis are inflammations of the nasal mucosa, eyes and skin, respectively, often due to allergens such as pollen, dust or other airborne substances.

Anaphylactic shock, the most severe form of allergy, is a medical emergency. It is often severe and sometimes can provoke a fatal systemic reaction in a susceptible individual upon exposure to a specific antigen (as wasp venom or penicillin) after previous sensitization. Anaphylactic shock is characterized by respiratory symptoms, fainting, itching, urticaria, swelling of the throat or other mucous membranes and a sudden decline in blood pressure. Symptoms of anaphylactic shock include dizziness, loss of consciousness, laboured breathing, swelling of the tongue, blueness of the skin, bronchospasm, low blood pressure, and death.

Inflammatory response syndrome (IRS)—is an inflammatory response to a wide variety of clinical insults. IRS occurs as a result of extensive tissue damage and necrosis or the invasion of microorganisms, with the release of chemical mediators or cellular by-products such as the cytokines, lipid metabolites and autocoids. These mediators can be released in response to tissues and cells affected by infections, shock (endotoxemia, blood loss, blunt trauma), hypoxemia, radiation, burns, organ transplants, graft rejections. The proinflammatory IRS response is primarily responsible for the development of organ dysfunctions, such as acute lung injury, acute respiratory distress syndrome (ARDS), damage to gastrointestinal dysfunction (ileus, changes in permeability, pancreatitis like problems), and dysfunctions of the kidney, heart, liver and brain.

Amino Acids: Abbreviations, Letter Code and Linear Structure Formula.

| Name | Abbr. | Linear structure formula |
| --- | --- | --- |
| Alanine | Ala A | CH3—CH(NH2)—COOH |
| Arginine | Arg R | HN=C(NH2)—NH—(CH2)3—CH(NH2)—COOH |
| Asparagine | Asn N | H2N—CO—CH2—CH(NH2)—COOH |
| Aspartic acid | Asp D | HOOC—CH2—CH(NH2)—COOH |
| Cysteine | Cys C | HS—CH2—CH(NH2)—COOH |
| Cyclohexylalanine | Cha Cha | Cha-CH2—CH(NH2)—COOH |
| Glutamine | Gln Q | H2N—CO—(CH2)2—CH(NH2)—COOH |
| Glutamic acid | Glu E | HOOC—(CH2)2—CH(NH2)—COOH |
| Glycine | Gly G | NH2—CH2—COOH |
| Histidine | His H | NH—CH=N—CH=C—CH2—CH(NH2)COOH |
| Isoleucine | Ile I | CH3—CH2—CH(CH3)—CH(NH2)—COOH |
| Leucine | Leu L | (CH3)2—CH—CH2—CH(NH2)—COOH |
| Lysine | Lys K | H2N—(CH2)4—CH(NH2)—COOH |
| Methionine | Met M | CH3—S—(CH2)2—CH(NH2)—COOH |
| N-Methyl-phenylalanine | NMeF NMeF | CH3-Ph-CH2—CH(NH2)—COOH |
| Norleucine | Nle Nle | CH3—(CH2)3—CH(NH2)—COOH |
| Norvaline | Nval Nval | CH3—(CH2)2—CH(NH2)—COOH |
| Phenylalanine | Phe F | Ph-CH2—CH(NH2)—COOH |
| Phenylglycine | Phg Phg | Ph-CH(NH2)—COOH |
| Proline | Pro P | NH—(CH2)3—CH—COOH |
| Serine | Ser S | HO—CH2—CH(NH2)—COOH |
| Threonine | Thr T | CH3—CH(OH)—CH(NH2)—COOH |
| Tryptophan | Trp W | Ph-NH—CH=C—CH2—CH(NH2)—COOH |
| Tyrosine | Tyr Y | HO-p-Ph-CH2—CH(NH2)—COOH |
| Valine | Val V | (CH3)2—CH—CH(NH2)—COOH |

L-amino acids are identified by capital letters (e.g. Tyr (Y)), whereas the corresponding D-isomeric form of the amino acid is identified by small letters (e.g. tyr (y)).

Salivary Gland Growth Factors, Hormones and Peptides: Regulation of Inflammation Over the last few decades salivary gland growth factors (such as epidermal growth factor; EGF) have gained increased recognition as playing an important role in tissue repair. Another important feature of the actions of salivary gland factors, which can be growth factors and hormones, is the regulation of oral and systemic immune and inflammatory responses (Mathison et al, 1994). It is apparent that salivary gland involvement in regulating systemic immune and inflammatory responses is under the control of the sensory, sympathetic and parasympathetic nervous systems, as well as endocrine control from steroid control and peptide hormones. One aspect of nervous system regulation of the salivary glands involves the "cervical sympathetic trunk-submandibular gland (CST-SMG) axis" (Mathison et al, 1994; 1993), which is a distinct neuroendocrine system that is involved in regulating inflammatory responses and systemic homeostatic mechanisms (Ramaswamy et al., 1989; Mathison et al, 1995). The release of hormones from other salivary glands (e.g. parotid, sublingual, etc.) are also under the control of the nervous system.

Perturbation of the CST-SMG axis, by either performing a cervical sympathetic denervation or by removing the submandibular glands, results in an enhanced hypotensive response to intravenously administered endotoxin (Mathison et al, 1993). This observation led us to postulate the existence of factors within the salivary glands that modulate endotoxic hypotension, and we subsequently isolated a seven amino acid peptide (sequence=Thr-Asp-Ile-Phe-Glu-Gly-Gly SEQ ID NO.1; TDIFEGG submandibular gland peptide-T (SGP-T)), which at doses as low as 1 $\mu$g/kg inhibits lipopolysaccharide induced hypotension (Mathison et al, 1997b). Investigation of structure activity relationship has identified the C-terminal of SGP-T, the tripeptide FEG (Phe-Glu-Gly) and its D-isomer feG, also have significant anti-inflammatory activities (U.S. patent application Ser. No. 051/395). The biological activities of SGP-T, FEG Or feG include: a significant reduction in the severity of intermediate hypersensitivity reactions in the lung (Dery et al., 1999, 2000; Befus et al, 2000a,b,c), intestine (Mathison et al, 1997b,c; 1998), heart (Turesin et al, 2000) and the cardiovascular system (Mathison et al, 1997a, 1999b, 2000b; Davison et al, 2000), inhibition of neutrophil chemotaxis (Mathison et al, 2000a) and superoxide production (Nkemdirim et al, 1998).

Inflammation

Inflammation is a defense reaction caused by tissue damage or injury, characterized by redness, heat, swelling, and pain. Inflammation is the result of a response of the body's defense system that localizes and normally eradicates the irritant stimulus and repairs the surrounding tissue. Inflammation is a necessary and beneficial process, and important for survival. The inflammatory response involves four major stages: 1. dilation of capillaries to increase blood flow; 2. microvascular structural changes and escape of plasma proteins from the bloodstream; 3. leukocyte and lymphocyte rolling, adhesion and transmigration through endothelium and accumulation at the site of injury; and 4. activation of biochemical processes designed to neutralize and eradicate the offensive stimulus and initiate tissue repair.

B.1. The Leukocyte and Lymphocyte Recruitment and Activation Cascade

The leukocyte (and by inference, the lymphocyte) adhesion cascade is a sequence of activation events that ends with extravasation of a leukocyte, whereby the cell exerts its effects on the inflamed site. At least five steps of the adhesion cascade are capture, rolling, slow rolling, firm adhesion and transmigration. Each of these five steps is necessary for effective white blood cell recruitment, because blocking any of them can reduce white blood cell accumulation in the tissue. At any given moment, capture, rolling, slow rolling, firm adhesion and transmigration all happen in parallel, involving different white blood cells in the same microvessels. Some anti-inflammatory agents function as blockers, suppressors, or modulators of the inflammatory response at specific points in this sequence of events which is a part of the inflammatory process. The principal clinical hallmarks of inflammation are: rubor (redness); dolor (pain); calor (heat—but only of skin and extremities); tumor (swelling); and functio laesa (loss of function). Redness is caused by increased blood flow to the site, due to the action of mediators, axon reflex, and local increase in the hydrogen ion concentration. Heat is also due to increased blood flow and greater local cellular metabolism.

Swelling is the result of increased blood flow, oedema, infiltration of cells, and the proliferation of connective tissue in subacute-to-chronic lesions. Pain is due to the effects of mediators on sensory nerves and the stretching of these nerves due to swelling. Loss of function is due to replacement of parenchymal tissue (e.g., damaged myocardium); reflexive disuse due to pain; and mechanical, as when a joint either swells during acute inflammation or scar tissue formation in a chronic lesion. Thus, the inflammatory response can viewed as is a dynamic, changing process and the longer the process continues the likelihood that irreversible alteration of parenchymal tissue (e.g., scarring) occurs increases.

An essential point of this application is regulation of the severity of immediate or Type 1 hypersensitivity (anaphylactic) reactions and their associated clinical conditions, the inflammatory response syndrome and other inflammations.

B.2. Selectins and Integrins: Their Role in Cell Adhesion and Activation

Adhesion receptors are involved in many leukocyte functions including haematopoiesis, migration, activation, mediator generation and apoptosis. The leukocyte adhesion receptors are involved in many biological processes such as allergic disease, other types of inflammation, wound healing, thrombogenesis, atherogenesis and embryogenesis.

The adhesion receptors have been primarily studied for their role in directing leukocyte migration through vascular endothelium, and are intimately involved in all the processes described in the leukocyte recruitment and activation cascade described above.

The leukocyte adhesion receptors comprise several large family of cell surface proteins including the selectins, integrins, immunoglobulins and their counter receptors. There are three selectins. E-selectin expressed on endothelium, P-selectin expressed by platelets and endothelium and L-selectin expressed on most leukocytes. L-selectin is constitutively expressed but shed on cellular activation as a result of the actions of a membrane bound metalloproteinase. The ligand for L-selectin on inflamed venular endothelium has not been identified, although L-selectin does bind to PSGL-1. The selectins mediate capture of leukocytes under flow conditions, and mediate the rolling of leukocytes on endothelial cells.

Integrins are receptor proteins which are of crucial importance as they facilitate and promote cell binding and responses to the extracellular matrix. Functional integrins consist of two transmembrane glycoprotein subunits that are non-covalently bound. Those subunits are called alpha and beta. The alpha subunits all have some homology to each other, as do the beta subunits. The receptors always contain one alpha chain and one beta chain and are thus called heterodimeric. To date, 16 alpha and 8 beta subunits have been identified, which combine in different ways to form 22 natural integrins. Integrins can adhere (bind) an array of ligands with common ligands being fibronectin and laminin.

Integrins are involved in a wide range of biological functions including maintenance of tissue homeostasis through binding to matrix proteins, and one of their more intensely studied functions is their involvement in leukocyte migration. The beta 2 (CD18) leukocyte integrins comprise four members CD11a–d/CD18. CD11a/CD18 (LFA-1) and CD11b/CD18 (Mac-1) are expressed on all leukocytes and are involved in a range of functions including transmigration through endothelium and cell activation. Three receptors for the integrins have been identified: ICAM-1 and 2 are expressed on endothelium and ICAM-3 expressed on most leukocytes. The beta 1 integrins (eg. the CD49 series) are also intimately involved in the biological function ascribed to the beta 2 integrins.

Tissue Specific Inflammation

C.1 The Respiratory System

Bronchial asthma is usually a chronic (long-term) disease affecting the bronchial tubes (bronchi, breathing tubes or airways) of the lungs and the symphtoms of asthma are the result of constriction or narrowing of irritable bronchial tubes. This constriction is caused by bronchial tube muscle spasm and narrowing due to inflammation, most frequently provoked by antigen induced release of histamine, leukotrienes and other chemical mediators from mast cells. With intrinsic asthma these mediators are released without an allergic trigger (i.e. following a cold or with exercise). The net result of the asthmatic attack is muscle spasm, inflammation, edema (swelling), and increased mucus production within the bronchi. The process generates symptoms within 15–30 minutes of exposure (immediate response) and which generally subside within an hour. In some individuals a delayed response (late phase reaction) occurs 3–4 hours following the immediate or initial response. It should be noted, however, that the timing of these reactions exhibit marked variability between patients and can be shorter or longer in onset and duration. The late phase reaction, which probably develops from an inflammatory reaction, may last many hours or days and is frequently associated with increased bronchial hyperreactivity or irritability rendering the individual sensitive to a variety of inhaled irritants. The pulmonary inflammation that develops with asthma is due to the influx of inflammatory cells into the lungs using the leukocyte adhesion cascade described previously.

Endotoxin and other pulmonary and systemic inflammations can also cause severe and prolonged lung inflammation. In sheep receiving intravenously LPS, pulmonary dynamic compliance was reduced 30 min post-LPS (Wheeler et al., 1990). This acute change in lung response probably reflects a rapid onset of LPS actions on circulating leukocytes and the endothelial cells of the pulmonary blood vessels with a consequent release of myoactive inflammatory mediators. It is possible that the mediators effecting changes in pulmonary dynamic compliance could also contribute to the delayed influx of cells into the lungs. Our own recent studies indicate that inflammatory reaction occurs for several days after the original endotoxic insult, as reflected in enhanced lung inflammation at 24 and 48 h after LPS administration and the enduring (at least 5 days) increase in the number of circulating white blood cells (Fialho de Aranjo et al., submitted for publication).

C.2 The Cardiovascular System

Endotoxin consistently results in a decrease in ventricular compliance in several animal species including humans, dogs and pigs. In rats with their submandibular glands removed endotoxin provokes a decrease in Pmax–dP/dt (a measure of ventricular compliance) (Mathison et al, 1999a). In vitro studies have shown that changes in heart function induced by LPS are reflected by in vivo alterations in myocyte function. In a variety of species, such as the guinea pig, the rabbit and the rat reduced myocardial contractility is develops in septic hearts. Endotoxemia also produces structural changes to the heart, such as enhanced stiffness of the septic myocardium due to a decrease in myocardial collagen, an increase in interstitial water and the shrinkage of the myocytes. These changes contribute to systolic and diastolic myocardial dysfunction and in particular to the reduced ventricular diastolic relaxation. The final effectors of endotoxin induced changes in heart function are unknown, but neutrophils and macrophages/monocytes do contribute to alterations in myocyte function.

Anaphylactic reactions also can cause modification of heart function and are associated with an increase in neutrophil influx into the heart tissue (Turesin et al, 2000). This inflammation of the heart is effected by the leukocyte adhesion cascade described previously.

C.3. The Intestine

A variety of inflammatory insults such as food hypersensitivities, allergies, proliferation of bacteria or the development of an excessive burden of resident bacteria can contribute to intestinal tissue injury and inflammation. For example, an intense allergic reaction or the response to ingested bacterial toxins through a variety of mechanisms—from release of tissue injuring enzymes to dramatic decrease in tissue blood flow—can produce pronounced changes in intestinal motility and cause extensive tissue damage, particularly to the intestinal mucosa. The immediate hypersensitivity response, designed to expel the offending substances through increasing intestinal motility and secretion, in certain cases produces a significant "collateral damage" to adjacent healthy tissues. The maintenance of coordinated smooth muscle activity and the integrity of the mucosal barrier is essential not only for proper functioning of the intestine but also for the maintenance of overall systemic health.

Other inflammatory insults may not produce such rapid and severe damage to the intestine as an allergic or an endotoxic reaction, but since they are generally of more prolonged duration (days to years), the progressive movement of inflammatory cells (neutrophils, monocytes and lymphocytes) into the intestinal tissues produces damage to healthy tissues that can compromise repair processes. These prolonged inflammatory insults can result in the development of severe and chronic inflammation apparent in such conditions as inflammatory bowel disease (IBD). Control of inflammation thus involves a delicate balance between containment and removal of the precipitating agent and minimizing the "collateral damage" while at the same time initiating tissue repair and regeneration.

The intestine is the major organ affected by shock in rodents, pigs and humans. The shock response occurs consequent to extensive pooling of blood in these organs. (Mathison et al, 1990), and associated poor blood flow to the intestine. The resultant decreased oxygen extraction (Nelson et al, 1988) along with the release of cytotoxic molecules from inflammatory cells results in extensive mucosal damage and causes the intestine to lose coordinated motility patterns or to become totally inactive (a condition know as ileus). The coordinated contractile activity of the intestinal smooth muscle, necessary for effective and efficient intestinal transit, also is disrupted (Hellstrom et al, 1997) resulting in prolonged periods of stasis. All these factors, through increased enteric bacterial proliferation and translocation (Carrico et al, 1985), can contribute to the evolution of further organ dysfunction and progression of the systemic inflammation and sometimes localized or generalized sepsis.

Eskanadari and coworkers (1997) showed that peritoneal sepsis also provoked an increase in IL6 and CD14 (the LPS receptor on macrophages) in the intestinal smooth muscle. Concomitant with these changes in cytokine and macrophage receptor profiles was a decrease in the myogenic response of jejunal circular muscle to the myotropic agent, bethanchol. The activation of macrophages by peritoneally injected LPS was associated with a rapid and transient expression on resident muscularis macrophages (apparent only at 1 hour, as revealed with LFA1 (CD11/CD18) (Eskandari et al, 1997). The peptide feG was shown to reduce the number of CD14 and CD11b positive macrophages in the muscle layer of the rat intestine (Mathison et al, 1999b, 2000b; Davison et al, 2000).

A Summary: Salivary Glands and the Regulation of Inflammatory Responses

New and effective methods are required for the maintenance of organ function in all forms of toxic reactions, whether caused by hypersensitivities to antigen, viruses, bacterial endotoxins and exotoxins, or fungi. The endogenous regulators of inflammation, produced in the salivary glands, have been demonstrated to be potent anti-inflammatory agents. Although their primary role is classically considered to be the regulation of inflammatory responses in the mouth, it is now apparent that these glandular factors have effects on the whole of the gastrointestinal tract and generalized systemic effects as well (Mathison et al, 1994; 1997). Salivary gland growth factors and small peptide hormones may be used to treat a variety of inflammatory disorders.

SUMMARY OF THE INVENTION

It has been discovered that novel compositions of matter, mainly analogues of the tripeptide FEG which consist of di- and tripeptides containing substituted L-amino acids and/or their optical isomers D-amino acids, are potent modulators of the inflammatory reactions precipitated by allergic and endotoxic reactions.

The invention is directed to a peptide of the formula:

or

wherein X is selected from the group consisting of H and acetyl; R.sub.1 is selected from the group consisting of D or L-phenylalanine; tyrosine; tryptophan; phenylglycine; Nor-methylphenylalanine; cyclohexylalanine; and norleucine; R.sub.2 is selected from the group consisting of D or L-glutamate; and aspartate; and in the case of peptide (I), R.sub.3 is selected from the group consisting of glycine; D or L-alanine; beta-alanine; valine; leucine; isoleucine; sarcosine; and gamma-aminobutyric acid or another aliphatic amino acid; and Y is selected from the group consisting of OH or NH.sub.2, except the dipeptides H-L-Phe-L-Glu-OH
H-L-Trp-L-Glu-OH
H-D-Phe-D-Glu-OH
H-D-Trp-D-Glu-OH.

In the peptide according to the invention, X can be hydrogen, R.sub.1 can be D-phenylalanine, D-tyrosine or D-tryptophan, R.sub.2 can be D-glutamate, R.sub.3 can be glycine and Y can be NH.sub.2 or OH.

The invention is also directed to a pharmaceutical composition containing a peptide according to the invention, wherein the peptide can be present in admixture with a pharmaceutically acceptable carrier. The peptide can be present in admixture with another therapeutically active agent.

A treatment schedule composed of daily or twice daily administrations of the peptides which can be administered for once or successive dosing over many days with medications that can be administered by inhalation, orally subcutaneously or intravenously, can be utilized. Appropriate pharmaceutically acceptable carriers can be used in treatment administration.

The invention is also directed to a method of modulating inflammatory reactions in an animal which comprises administering to the animal a peptide according to the invention in an amount ranging from about 0.1 to about 1000 ig/kg. and a method for the treatment of allergic disorders in an animal using pharmaceutical compositions according to the invention. The disorder can be an intestinal allergy, asthma, rhinitis, an anaphylactic reaction. The animal can be a human being.

The invention is also directed to a method for the treatment of a toxic immunological reaction using pharmaceutical compositions according to the invention. The toxic immunological reaction can involve products released or on the surface of Gram-negative bacteria, Gram-positive bacteria, fungi, viruses or parasites. The immunological toxic reaction can involve inflammation of the respiratory system, inflammation of the gastrointestinal tract, inflammation of the heart or cardiovascular system, or inflammation of the skin, eyes and kidneys.

The invention also pertains to a method of manufacturing a medicament using a peptide according to the invention, in an amount effective to produce an therapeutic response.

The peptide can be selected from the group consisting of: peptide #1 H-D-tyr-D-glu-Gly-OH; peptide #2 H-D-trp-D-glu-Gly-OH; peptide #3 H-D-NMef-D-glu-Gly-OH; peptide #4 H-D-cha-D-glu-Gly-OH; peptide #5 H-D-nle-D-glu-Gly-OH; peptide #6 H-D-phe-D-glu-Gly-NH.sub.2; peptide #7 H-D-tyr-D-glu-Gly-NH.sub.2; peptide #8 H-D-trp-D-glu-Gly-NH.sub.2; peptide #9 H-D-NMef-D-glu-Gly-NH.sub.2; peptide #10 H-D-cha-D-glu-Gly-NH.sub.2; peptide #11 H-D-nle-D-asp-Gly-NH.sub.2; peptide #12 H-D-tyr-D-glu-OH; peptide #13 H-D-trp-D-glu-OH; peptide #14 H-D-NMef-D-glu-OH; peptide #15 H-D-cha-D-glu-OH; peptide #16 H-D-nle-D-glu-OH; peptide #17 H-D-phe-D-glu-NH.sub.2; peptide #18 H-D-tyr-D-glu-NH.sub.2; peptide #19 D-trp-D-glu-NH.sub.2; peptide #20 H-D-NMef-D-glu-NH.sub.2; peptide #21 H-D-cha-D-glu-NH.sub.2; peptide #22 H-D-nle-D-asp-NH.sub.2.

DRAWINGS

In drawings which illustrate specific embodiments of the invention, but which should not be construed as restricting the spirit or scope of the invention in any way:

FIG. 1 illustrates in tabular format data of the effects of C-terminus substitutions, N-terminus substitutions, aromatic substitution at position 1, and Asp substitution at position 2 in both L and D forms in FEG, and removal of the glycine on inhibition of intestinal anaphylaxis in vitro.

FIG. 2 illustrates in bar graph format data that the tripeptide YEG is an antagonist of the inhibitory actions of the general formula A peptide of the formula (I) XEG; X is an aromatic amino acid such as D-phenylalanine (feG) or L-Nor-methylphenylalanine (NMeF)EG, but is not an aliphatic amino acid such as L-Cyclohexylalanine or L-Norleucine. The results are presented as the mean±SEM. The number of animals is from 6 to 8. Significance: *P<0.05; *P<0.02.

FIG. 3a illustrates in bar graph format data of the inhibition by SGP-T, FEG and feG, of intestinal motility disturbances caused by intravenous endotoxin. The results are presented as the mean±SEM. Number of animals=3 to 15. Significance: *P<0.05; *P<0.01 when compared to saline treated control.

FIG. 3b illustrates a graphical depiction of the dose-dependent inhibition by feG and feG($NH_2$) of intestinal motility disturbances caused by intravenous endotoxin. The results are presented as the mean±SEM. Number of animals =8 to 10. Significance: *P<0.05; *P<0.01 when compared to saline treated control.

FIG. 4 illustrates two bar graph depictions of data regarding inhibition by feG of leukocyte accumulation in peritonal lavage fluid following intraperitoneal injection of lipopolysaccharide (LPS). Total and differential cell counts in peritoneal lavage of rats receiving intraperitoneal administration of lipopolysaccharide (LPS; 2 mg/kg ip (A) or 20 μg/kg iv (B)) with and without intraperitoneal treatment with feG (100 μg/kg). Levels of significance: *greater than saline P<0.05; #less than LPS P<0.05; n=4 to 6.

FIG. 5 illustrates two bar graph depictions of data regarding inhibition by feG of leukocyte accumulation (ED9 marker) and activation (CD18 marker) in the jejunal smooth muscle of rats following intraperitoneal injection of lipopolysaccharide (LPS). Number of positive interstitial cells in the muscle layers of the jejunum of rats receiving either 2 mg/kg of LPS intraperitoneally (A) or 20 μg/kg of LPS intravenously (B) with and without intraperitoneal treatment with feG (100 μg/kg). Number of cells per 40× field. Significance: *P<0.05 greater than saline; #P<0.05 less than LPS; n=4 to 6.

FIG. 6 illustrates in bar graph format data that the tripeptide feG inhibits the histarnine induced wheal response in the skin. The results are presented as the mean±SEM. Number of animals=8 to 10. Significance: *P<0.05; *P<0.01 when compared to saline treated control.

FIG. 7 illustrates the effects of feG on the binding of leukocytes to atrial slices.

FIG. 8 illustrates in bar graph format data regarding the time course of the oral feG administration on pulmonary inflammation occurring 24 hours after exposure to aerosolized 5% ovalbumin.

FIG. 9 illustrates a plot of data regarding the inhibitory effect of feG on allergen induced hyperresponsiveness to methacholine. feG as administered at a dose of 1 mg/kg orally. *P<0.05 by ANOVA.

FIG. 10 illustrates in bar graph format data about the prevention by feG of the blood neutrophilia caused by an anaphylactic reaction in Hooded-Lister rats. The results are presented as the mean±SEM. Number of animals=3 to 7. Significance: *P<0.05.

FIG. 11 illustrates in tabular format data regarding inhibition of the platelet activating factor (PAF) induced expression of CD11b and CD16b expression on human neutrophils by di- and tripeptides. Data represents mean±SEM for number of experiments shown in parenthesis. Significance: *P<0.05.

FIG. 12 illustrates a graphical depiction of data regarding inhibition by yeG of platelet activating factor (PAF) induced expression of CD11b on human neutrophils. Data represents mean±SEM of 7 experiments for yeG and 3 experiments for YEG. Significance: *P<0.05 for yeG; #P<0.05 for YEG.

DETAILED DESCRIPTION OF THE INVENTION

The present invention is concerned with the tripeptide feG (H-D-phe-D-glu-Gly-$NH_2$) described in U.S. patent application Ser. No. 09/051,395 and analogues of feG (peptides 1 to 11), the contents of which are incorporated herein by reference, as regulators of inflammatory cell function which reduces the reactivity of smooth and cardiac muscle to inflammatory stimuli. The present invention also includes compositions containing such immunomodulatory peptides and the use of such peptides and compositions as immunomodulators and regulators of smooth and cardiac muscle activity, either directly or indirectly.

EXAMPLE 1

Effects of the Peptides on Antigen Induced Contraction of the Sensitized Rat Ileum.

The Biological Response. The addition of antigen (OA) induced a slow tonic contraction of the intestinal (ileal) segments which peaked within 2 to 3 minutes before slowly receding to the baseline tension over 4 to 5 minutes. Urecholine (URE) produced a rapid tonic contraction that reached its maximum in 10 to 15 seconds. The tripeptide analogues did not alter the contractile response to URE (not shown), which allowed the use of the OA/URE ratio as a measure of the anti-anaphylactic responses of the peptide. The OA/URE ratio in untreated tissues was 0.26±0.02, which indicates that the sensitizing antigen caused a contractile response that was 26% of that of urecholine. When FEG was added to the bath the OA/URE ratio was only 0.12±0.04, or 44% of the control response.

Essential Structural Determinants. Analogues of FEG were designed to determine the importance of the carboxyl and amino-terminal groups as well as the amino acid in position 2 to biological activity. Acetylation (Ac-FEG) or amidation of (FEG-$NH_2$) caused a loss of biological activity (FIG. 1), indicating that a N-terminus amide and a C-terminus carboxyl group are required for biological activity. Substitution of small non-aromatic residues in position 1, by substituting the Phe (F) with Ala (A) (AEG) and Gly (G) (GEG), resulted in a loss of biological activity, whereas large aliphatic residues such as Cha and Nle were tolerated. These results suggest that either aromaticity or substantial hydrophobicity of the first residue is necessary for biological activity. The distance of the carboxyl residue at position 2 was also important, as substitution of Asp (D) for Glu (E) (FDG), a decrease of a single carbon in chain length, caused a loss of biological activity.

Substitutions in Position 1 and 2 and D-Enantiomeric Substitutions: Limited aliphatic substitutions can be made in position 1 and substitutions with cyclohexylalanine (ChaEG) and norleucine (NleEG) being tolerated. On the other hand, not all aliphatic substitutions in position 1 yielded active peptides since leucine, isoleucine and norvaline, which have limited projection into space because of the methyl and methylene groups.

FEG, and its d-enantiomer feG both significantly attenuated the antigen induced contraction of the terminal ileum (FIG. 1). The substitution of Trp (W) for Phe, in the analogue WEG, also significantly reduced antigen induced contractility, but unlike feG, the d-enantiomer of WEG, weG lacked activity. The substitution of Tyr (Y) for Phe, giving the analogue YEG, resulted in a loss of biological activity. However, yeG was as potent as FEG in inhibiting antigen induced contractions of the ileum. Both FDG and YDG were inactive, whereas WDG was active. All analogues containing the D-enantiomer of Asp (fdG, ydG, and wdG) were inactive. Several other aromatic substitutions were permitted and these include phenylglycine (PhgEG) and Nor-methylphenylalanine (NMeFEG).

Several dipeptides were found to reduce antigen induced contraction of sensitized ileal tissues. The active peptides were FE, fe and (cha)e.

While we do not wish to be bound by any theories, adverse or otherwise, we have concluded from structure-activity relationship considerations that four components of the tripeptide FEG were found to be optimal for the biological activity of this peptide:

an aromatic ring or an aliphatic substitution in position 1,
a carboxylic acid on the side chain of position 2 that is separated from the peptide backbone by two methylene groups,
a free amino terminus, and
a free carboxyl terminus.

The only exception to these general rules was observed with the substitution of an Asp for a Giu in position 2 in the analogue WDG. Another feature of the active peptides was that combination of D-amino acid substitutions at position 1 (D-Phe and D-Tyr) and at position 2 (D-Glu) as in feG and yeG were tolerated, while the D-Asp substitution at position 2 resulted in inactive analogues. In addition, the third aliphatic amino acid is not essential for biological activity since removal of the terminal glycine yielded dipeptides that possess biological activity.

An important aspect of these studies, in view of previous investigations with the tripeptides feG and FEG (U.S. patent application Ser. No. 095/051,395, the subject matter of which is incorporated herein by reference) is that identification of active peptides were not obvious from the structure activity relationship studies. The major findings related to the novelty (nonobviousness) is that FEG and feG inhibit antigen induced contraction of the intestinal tissue, whereas when tyrosine was substituted into position 1, the D-isomeric analogue (yeG) possessed this biological activity. However, the L-isomeric analogue (YEG) was inactive. Furthermore, YEG was found to be an antagonist since this peptide inhibited the actions of tripeptides with an aromatic substitution in position 1, but was ineffective against those with an aliphatic substitution in position 1 (FIG. 2). FIG. 2 demonstrates that the tripetide YEG is an inhibitor of the anti-anaphylactic actions of tripeptides on the rat ileum. The inhibited tripeptides are of the general formula X-R.sub. 1 -R.sub.2 -R.sub.3 -Y wherein X is selected from the group consisting of H, R.sub.1 is an aromatic residue, R.sub.2 is a D or L-glutamate; R.sub.3 is an aliphatic amino acid selected from the group consisting of glycine D-alanine, and Y is an OH group. Furthermore, it was neither obvious that aliphatic substitutions in position 1 of tri- or dipeptides would possess biological activity nor that asparate substitutions would be tolerated in position 2 in some peptides.

EXAMPLE 2

Inhibition of Intestinal Motility Disturbances Caused by Intravenous Endotoxin

The migrating motor complexes (MMCs; Scott & Tan, 1996) in fasted rats exhibit an intrinsic rhythmicity with a cycle period of 11.6 ±1.8 min, which was not affected by treatment with the peptides. Intravenous injection of LPS at either 10 or 20 $\mu$g/kg disrupted the normal fasting pattern of intestinal MMCs into the characteristic fed pattern which persisted for 85±3 min (n=3) and 105±8 min (n=15), respectively. The disruptions in the MMCs developed within 20±4 min and 17±1 min for the respective 10 and 20 $\mu$g/kg doses of LPS. The 20 $\mu$g/kg dose of LPS was used for subsequent experiments.

Intravenous FEG and oral feG, at a dose of 100 $\mu$g/kg 20 min before LPS injection, significantly inhibited the duration of LPS disrupted intestinal MMCs, whereas this dose of SGP-T was ineffective (FIG. 3a). An intravenous dose of 350 $\mu$g/kg of SGP-T, however, significantly reduced the duration of MMC disruption, but was still less effective than either of the two tripeptides. The tripeptide feG dose-dependently inhibited the duration of MMC disruption with 65 $\mu$g/kg providing optimal inhibition (duration of disruption 26±9 min), whereas 10 $\mu$g/kg of the peptide was ineffective (FIG. 3b). Replacement of an oxygen molecule on the C-terminal glycine with an amide (NH2) yielded a peptide (feG(NH2)) that was very potent in inhibiting LPS induced disruption of the MMCs (FIG. 3B).

EXAMPLE 3

Inhibition by feG of Endotoxin Induced Leukocyte Accumulation in the Peritoneum

Intraperitoneal feG, which itself did not affect the total number of cells in the peritoneum, significantly reduced the total number of cells recovered in peritoneal lavage fluid consequent to LPS treatment.

LPS, injected intraperitoneally (2 mg/kg) or intravenously (20 $\mu$g/kg) 18 h before sampling the perioneal cavity, elicited a 3-fold increase in the total number of cells recovered from the peritoneum (FIG. 4). Intraperitoneal feG, which itself did not affect the total number of cells in the peritoneum, significantly reduced the total number of cells recovered, as well as the number of macrophages and neutrophils, recovered in peritoneal lavage fluid in animals injected with LPS.

EXAMPLE 4

Inhibition by feG of Endotoxin Induced Leukocyte Accumulation and Activation in Jejunal Smooth Muscle Eighteen hours after the intraperitoneal (2 mg/kg) or intravenous (20 $\mu$g/kg) injection of LPS increased the number of macrophages and neutrophils expressing the ED9 antigen in the muscle of the small intestine. The expression of this antigen was not altered relative to saline treated controls (FIG. 5). Whereas feG in the absence of the LPS treatment did not affect the increase in tissue macrophages expressing the ED9 antigen, it prevented LPS induced expression of this antigen on tissue neutrophils. The number of leukocytes expressing the cell activation marker, CD18, which was increased 4 to 6-fold by intraperitoneal LPS, was decreased by more than 50% by intraperitoneally administered feG. The LPS (2 mg/kg) induced increased, by 3-fold, of the number of leukocytes expressing the inducible LPS-receptor marker CD14, was also reduced significantly by feG (not shown).

EXAMPLE 5

Inhibition by feG of Histamine Induced Wheal Response in the Skin

The injection of histamine intradermally causes an increase in vascular permeability with an associated leakage of fluid and protein into the surrounding tissue. The leak of albumin is visualized by labeling it with a Evans blue dye, such that site of protein leakage is visable due to a bluing of the skin. This leakage is the wheal response. When 50 il of histamine (10–4M) was injected into the skin of rats a wheal response of 4.2 mm was elicited (FIG. 6). The tripeptide feG when injected intradermally into the skin at the same site that the histamine was subsequently injected (10 min later) an inhibition,of the wheal was noted. A significant inhibition of the histamine wheal reaction was noted with feG in the dose range of 10–13 to 10–11 moles (FIG. 6).

EXAMPLE 6

Inhibition by feG of Leukocyte Adhesion to Atrial Tissue

To examine the effects of the tripeptide feG on leukocyte adhesion to tissues tissue sections from the atrium of Sprague-Dawley rats were prepared and then incubated with leukocytes isolated from the same strain of rats. Addition of PAF (10–9M) to the leukocytes doubled the number of cells binding to the atrial slices from 6.2±1.0 to 12.2±2.2 (FIG. 7). The tripeptide feG, at a dose of 10–9M, when incubated with isolated, rat leukocytes significantly inhibited the PAF stimulated adhesion of the leukocytes to the atrial tissues, but did not modify basal adhesion, measure in the absence of PAF.

EXAMPLE 7

Inhibition by feG of Allergen Induced Pulmonary Inflammation

Brown-Norway rats respond to an aerosol challenge with 5% sensitizing antigen ovalbumin (OA) with a substantial pulmonary inflammation at 24 h (FIG. 8). The effect of time of administration of feG on the the allergen induced pulmonary inflammation was investigated. feG (1 mg/kg) significantly reduced the the total cell number recovered from the airways when administered −30 min to +6 h following allergen challenge. The number of macrophages was reduced when feG was administered prior to (−30 min) and at +30 min after exposure to allergen. However, the protective effect of feG against influx of neutrophils and eosinophils into the airways was observed even if the peptide was given 6 h following challenge.

EXAMPLE 8

Inhibition by feG of a Late Phase Hypersensitivity Reaction in the Lungs

When sensitized Brown-Norway rats are challenged with methacholine a dose of 9.7±1.5 mg/ml caused a 200% increase in airways resistance (Raw) (FIG. 9). With sensitized rats that had received an aerosol challenge of 5% OA 24 h previously the rats became hyperresponsive to methacholine since a significantly lower dose of methacholine (6.7±0.7 mg/ml) elicited a 200% increase in RAW. However, in rats that had been treated with 1 mg/kg of feG orally 30 min prior to the allergen challenge the hyperresponsive response was abolished since the 200% increase in RAW was reversed and 9.4±1.1 mg/ml of methacholine was required to increase RAW by 200%. Rats treated with feG, but not the allergen, were less responsive to methacholine, since a larger dose (14.8 mg/ml) of methacholine was required to elicit the 200% increase in RAW.

EXAMPLE 9

Inhibition by feG of Blood Neutrophilia Caused by an Immediate Hypersensitivity Reaction The sensitization of Hooded-Lister rats to ovalbumin did not affect the number of circulating neutrophils (FIG. 10). However, 3 hours after the intragastric administration of the antigen (ovalbumin) to sensitized rats, a significant blood neutrophilia was observed. This increase in the number of circulating neutrophils was prevented by the intraperitoneal administration of the tripeptide feG (100 $\mu$g/kg).

EXAMPLE 10

Inhibition of the Platelet Activating Factor (PAF) Induced Expression of CD11b and CD16b Expression on Human Neutrophils by Di- and Tripeptides The expression of CD11b and CD16b on the surface of neutrophils are represented as the difference in the mean fluorescence intensity (MFI) measured in cells incubated in the presence of PAF alone and those incubated with 10–11M concentration of peptide and PAF. Many of the tripeptides reduced the expression of CD11b and CD16b on human neutrophils that had been stimulated with platelet activating factor (PAF; 10–9M). The results are shown in FIG. 11.

CD11b expression was inhibited by feG, yeG and FEa. The modification of this integrin appears to prefer peptides with D-amino acid substitutions in positions 1 and 2, and an aromatic residue in position 1.

CD16b expression detected by CD16a.FITC was altered by a larger number of peptides. Peptides with either an aromatic D- or L-phenylalanine in position 1, or an aliphatic (cyclohexylalanine or Norleucine) substitution in position 1 were active. The dipeptide, fe, was also active. Two amidated peptides, feG(NH2) and (cha)e(NH2) reduced CD16 a expression.

CD16b expression detected by CD16b.FITC was reduced by a selected set of tripeptides with an aromatic amino acid in position 1 which could be either D-phenylalanine (f), L-phenylglycine (Phg), or L-Nor-methylphenylalanine (NMeF). Two dipeptides reduced CD16b expression, fe and (cha)e.

EXAMPLE 11

Inhibition by yeG of CD11b Expression on Human Neutrophils, But Lack of an Effect of YEG The increase in CD11b expression of 118±22% on human neutrophils elicited by platelet activating factor (PAF; 10–9M) was reduced to 72±14%, 59±14% and 68±13% by 10–12M, 10–11M and 10–10M concentrations of yeG. On the other hand YEG was not effective in this concentration range, and decrease to 80±12% was only seen with 10–8M of the peptide (FIG. 12).

SUMMARY OF THE INVENTION

The present invention describes novel peptide analogues of feG that also exhibit potent anti-inflammatory actions.

Using feG as a prototype molecule it is apparent that these peptides inhibit the inflammatory reaction by interfering with the "Leukocyte and Lymphocyte Recruitment and Activation Cascade". It is known that SGP-T, the parent heptapeptide, prevents the rolling of leukocytes on mesenteric venules induced by LPS and histamine (Mathison et al, 1999), and this invention reveals that peptides other than SGP-T also reduce leukocyte adhesion (FIG. 7), extravasation (FIG. 4) and activation of tissue resident or migratory leukocytes (FIG. 5) in the targeted tissue. Consequent to these activities feG and its analogues have potent actions that reduce tissue inflammation (FIGS. 4 and 5), and prevent inflammation induced activation of targeted tissues such as the intestine (FIG. 3A & 3B), skin (FIG. 6), the lungs (FIG. 9) and the bone marrow (FIG. 10). These anti-inflammatory actions may be partly mediated through the alteration in the expression of the leukocyte adhesion molecule CD11b (FIG. 11 & 12) or the expression of CD16b (FIG. 11). The tripeptide yeG, which like feG is a potent inhibitor of antigen induced contraction of the sensitized rat intestine (FIG. 1), reduced PAF induced expression of CD11b.

Restrictions on the amino acid substitutions that are tolerated in analogues of FEG/feG are described (see EXAMPLE 1), although a theory for the rational substitution of amino acids into the peptides that permits the prediction of biological activity of specific peptides is not apparent. For example, it is not obvious which aromatic or aliphatic substitutions in position 1 of tri- or dipeptides would possess biological activity in the four assays examined (antigen induced contraction of the sensitized ileum, and alteration of PAF induced expression of CD11b or CD16b on human neutrophils; FIGS. 1 and 12). An important observation is the demonstration that some C-terminal amidated peptides are very potent, being effective in the picomolar to nanomolar range (FIG. 3 and FIG. 12).

DESCRIPTION OF METHODS USED IN EXAMPLES

EXAMPLE 1

Effects of the Peptides on Antigen Induced Contraction of the Sensitized Rat Ileum Effects of C-terminus substitutions, N-terminus substitutions, aromatic substitution at position 1, and Asp substitution at position 2 in both L and D forms in FEG, and removal of the glycine on inhibition of intestinal anaphylaxis in vitro.

In this in vitro motility study analogues of the tripeptide FEG were examined for their inhibitory effects on an anaphylactic reaction provoked by antigen on intestinal segments isolated from ovalbumin sensitized rats. The procedures described by Mathison et al. (1997a) were followed with slight modifications. Sprague-Dawley rats were sensitized to 1 mg ovalbumin (OA) and 50 ng pertussis toxin (Sigma Chemical, St. Louis, Mo.) (Kosckea et al, 1994). Four to six weeks following sensitization, the terminal ileum was excised and 2 cm sections were mounted in 20 ml organ baths under 0.75 g of tension and the isometric force generated by OA and urecholine (Frosst, Kirkland, QC) was measured using a Grass Force Displacement Transducer FT03 (Quincy, Mass.). The tissues were washed several times in Krebs and allowed to equilibrate for 15 minutes. Anti-anaphylactic properties of FEG and its analogues were determined by adding 10 ig of peptide to a bath and incubating for 10 min. Tissue segments were washed, the baseline reestablished, and then challenged with 1 mg of the OA antigen. OA contractile response was measured at peak contraction. Tissues were washed and peak contractile response obtained by adding $10^{-5}$M urecholile. The mucosa was then scraped from the tissue, the mass of the remaining muscle determined, and the tension calculated in gram force per gram wet tissue. Results were expressed as the ratio of OA induced contractile response to urecholine induced contractile response. To obtain the relative activity the OA/URE ratio for each peptide was expressed as a percent of control.

In several studies we examined the ability of YEG to act as an antagonist of the inhibitory activity of some of the peptides that reduced the magnitude of antigen induced contraction of the sensitized rat ileum. For these studies YEG was added to the tissue bath 10 minutes before adding a biologically active peptide, and the experiment was then performed as described above.

EXAMPLE 2

Inhibition of Intestinal Motility Disturbances Caused by Intravenous Endotoxin

Intestinal Motility. Male and female Sprague Dawley rats, weighing 200–250 g were raised at the Life and Environmental Sciences Animal Resource Centre, The University of Calgary. The rats were maintained with lights on from 7:00 to 19:00 h, and were provided food and water ad libitum. For the intestinal motility experiments lipopolysaccharide (LPS; Salmonella typhosa; Sigma Chemical Co., St. Louis, Mich.) was injected intravenously at a dose of 20 µg/kg (Helistrom et al, 1997).

For motility recording rats were surgically prepared, as previously described (Mathison et al, 1998), with three bipolar jejunal electrodes under halothane anesthesia following an 18 h fast. A plastic cannula, with three pairs of Teflon-coated stainless steel bipolar electrodes, was positioned in an intrascapular region. The wires were subcutaneously tunnelled to the anterior abdominal wall, entering the peritoneal cavity through a stab incision. The electrodes were fixed in the muscle of the jejunum at 2.5 cm intervals, with the first pair placed 2.5 cm from the ligament of Treitz. The electrodes of each pair were sutured 3 mm apart for bipolar recording. In some rats indwelling jugular catheters were installed for subsequent administration of peptides. After surgery, the rats were given oral fluids for 24 h before returning them to a regular diet. On the day 7 after surgery the rats were fasted overnight and the next day, after stabilization in the recording chamber, the three pairs of electrodes were connected to bioelectric amplifiers (Hewlett-Packard, model 8811A) with upper and lower cut-off values of 0.05 and 300 Hz respectively for recording jejunal myoelectric activity. An eight-channel chart recorder (Hewlett-Packard, model 7858A) simultaneously recorded the electric signals generated by the migrating myoelectric complexes (MMCs), for three cycles before and 120 min after intravenous challenge with 20 µg/kg of LPS. SGP-T, FEG and feG were given intravenously via an indwelling jugular catheter, although feG was also given orally with a feeding needle 20 min before injecting LPS intravenously. The LPS was injected via the penile vein while the rats were briefly anesthetized with halothane.

Changes in intestinal motility were detected by modifications in jejunal myoelectric activity from the standard MMCs that occur in fasting animals to a totally disrupted pattern of intense, irregular myoelectric electricity that developed with the endotoxic reaction. Before and after challenge with LPS, the cycle period of MMCs was determined by measuring the time between the ends of phase III activity (the marked increase in regular phasic myoelectric and motor activity) of successive MMCs.

EXAMPLE 3

Inhibition by feG of Endotoxin Induced Leukocyte Accumulation in the Peritoneum Male and female Sprague Dawley rats, weighing 200–250 g were raised at the Life and Environmental Sciences Animal Resource Centre, The University of Calgary. The rats were maintained with lights on from 7:00 to 19:00 h, and were provided food and water ad libitum. To study cell surface markers on intestinal immunocytes extravasation into the pertoneum the LPS was injected either intraperitoneally at a dose of 2 mg/kg or intravenously at 20 µg/kg.LPS, injected intraperitoneally (2 mg/kg) or intravenously (20 µg/kg), elicited a 3-fold increase in the total number of cells recovered from the peritoneum (FIG. 3).

Rats were pretreated with LPS and/or feG and 18 h later cells were recovered by peritoneal lavage by injecting 10 ml of 0.9% saline into the peritoneal cavity. The abdomen was massaged and an incision was made to allow removal of all fluid in the cavity. The cells were spun down (200 g) and resuspended in 10 ml of lysis buffer (NH4C1) for 5 min to lyse red blood cells. Cell viability was evaluated by determining Trypan Blue exclusion. Differential counts were determined with cells stained with modified Wright stain. The dilutions of the primary and secondary antibodies are indicated for histochemistry and FACS analysis, respectively: ED9 (1:100 & 10 µl of 1:10) MAb mouse anti-rat resident macrophage ED9; mouse anti-rat CD14 (1:50 & 10 µl neat); CD18 (1:100 10 µl of 1:50).

EXAMPLE 4

Inhibition by feG of Endotoxin Induced Leukocyte Accumulation and Activation in Jejunal Smooth Muscle Intestinal histochemistry. Rats were injected with LPS either intraperitoneally (2 mg/kg) or intravenously (20 µg/kg) and/or intraperitoneally with feG (100 µg/kg) 18 h prior to removing the tissues. Whole mounts of midjejunal tissue were pinned and fixed in paraformaldehyde for 20 min at ~150% of resting tissue length and ~250% of resting tissue diameter. After fixing, the tissues were stripped of their mucosa, and histochemistry was performed on the muscularis. The mounted mesentery or pinned tissues were incubated for 24 h at 4° C. with the primary antibody (either ED9, CD14 or CD18) followed by three 5-min washes in 0.05M phosphate buffered saline (PBS). The tissues were then incubated with a labeled secondary antibody (goat anti-mouse FITC for fluorescence or goat anti-mouse coupled to biotin) at 4° C. overnight and washed three times for 5 min in 0.05M PBS. The HRP labeled antibody was detected using the diaminobenzadine (DAB) reaction. For control experiments the primary antibody were excluded, although the tissues were still incubated with the secondary antibody. The intestinal tissues were then dry mounted on chrome alum coated slides and coverslipped for viewing under a fluorescent microscope and viewed at ×200 magnification. Counting was performed blind and the number of labeled cells determined in four random fields of each specimen. The dilutions of the primary and secondary antibodies for histochemistry were: ED9 (1:100) MAb mouse anti-rat resident macrophage ED9; mouse anti-rat CD18 (1:100). The ED9 labeled cells were distinguished as neutrophils or macrophages based on their morphology and nuclear structure.

EXAMPLE 5

Inhibition by feG of Histamine Induced Wheal Response in the Skin

Male, Sprague-Dawley rats (Biosciences, The University of Calgary) weighing 250–350 g were used. Rats were anaethetized with sodium pentobarbital (65 mg/kg) and their backs shaved. A 2×4 grid was drawn on the back in black ink and in the middle of each square different concentrations of peptide (10–16 to 10–9 moles) in 50 µl were injected intradermally. Saline was used as a control. The animals were then injected, via the penile vein, with Evans blue (20 mg/kg), a dye that binds to albumin. Ten minutes after the first intradermal injection 50 µl of histamine (10–4M) was injected into a closely adjacent site. Within a few minutes of the histamine injection into a control site, a blueing of the skin begins to develop as the Evans Blue-albumin complex moves out of the blood vessel consequent to the histamine injection. Ten minutes after the injection of histamine the size of the histamine induced wheal was measured using calipers.

EXAMPLE 6

Inhibition by feG of Leukocyte Adhesion to Atrial Tissue

Male, Sprague-Dawley rats (Biosciences, The University of Calgary) weighing 250–350 g were used. Rats were intraperitoneally injected with LPS (2 mg/kg), feG (100 µg/kg) or both LPS and feG 18 h prior to removing the tissues.

Lipopolysaccharide (*Salniiioella typhosa*) was purchased from the Sigma Chemical Co., St. Louis, Mich., USA. feG was synthesized at The University of Calgary, and the composition of each synthesis was verified by amino acid analysis. The primary antibody (CD18 (1:100 10 µl of 1:50)) was purchased from Serotoc, Canada) and diluted as recommended for histochemistry.

Leukocyte preparation and use. Blood was obtained by cardiac puncture from rats anesthetized with halothane into a 10 ml syringe. The blood was allowed to clot, the serum decanted free and centrifuged at 300×g for 10 min @20° C. The leukocytes were resuspended in lysis buffer (NH4C1) for 5 min to lyse red blood cells, washed twice with 15 ml of PMN buffer prior to use. When cell surface markers well examined with the fluorescent activated cell sorter (FACScan Becton Dickinson Immunocytochemistry Systems) the appropriate primary antibodies were added to the cells for 20 min at room temperature. The cells were washed with 1 ml of PMN buffer and the secondary antibody added for another 20 min incubation at room temperature. After a final wash the cells were analyzed with a FACScan.

Leukocyte adhesion assays. To examination leukocyte adherence to atrial tissues the cells were prepared as described above, except the antibody labeling was not performed after the adhesion assay until the cells had adhered to the tissues. Cryostat sections of the atrium were prepared from hearts perfused with 4% paraformaldehyde or 0.9% saline and laid onto chrom-alum coated slides and fixed with 50% acetone before processing for histochemistry. The acetone fixation assures that the atrial slices remain attached to the slides during the adhesion and immunochemical procedures. Leukocytes were prepared as described above, and 350 µl of a 1×10⁶ cells/ml were added to the slides holding the atrial sections, and allowed to sit for 30 min. In some experiments the slides were slowly agitated at 3 rpm to mimic low sheer forces. After adhesion the slides were washed twice with PMN buffer, and the leukocytes fixed to the atrial sections with 50% acetone. CD18 antibody (1:50) was added to the slides and and incubated for 1 hour. After a series of three washes goat antimouse biotinylated secondary antibody (1:200;350 µl/slide) was added for a 2 h incubation at room temperature. The antibodies were visualized using the antibody biotinylated complex assay (Vector Laboratories, Burlingame, Calif.) performed according to manufacturer's instructions with a 30 min incubation with the ABC complex and a 1 to 2 min incubation with the diaminobenzadine (DAB) solutions. After a series of three 5 min washes, the slides were dried, coverslipped and the number of leukocytes adhering to three atrial sections/ slide counted under a 40× objective. The data is represented as the number of leukocytes/40× field.

EXAMPLE 7

Inhibition by feG of Allergen Induced Pulmonary Inflammation

The Brown Norway rat/ovalbumin sensitization model of allergic asthma was used. These rats are high IgE producers and and are widely used to study asthma because they develop an early and a late phase bronchoconstriction, as well as an increase in bronchial hyperresponsiveness.

Brown Norway rats (10–12 weeks old) are sensitized to ovalbumin (OA; Sigma Chemical Co. St. Louis, Mich.) with a 1 ml 0.9% saline ip injection containing 10 µg OA, 15 mg Al(OH)3 (ICN, Aurora, Ohio) and 50 ng $B.$ $pertussis$ toxin (Sigma). Twenty-one days post sensitization rats were given either an oral feG treatment (1000 ug/kg) or a saline sham treatment under light anaesthesia. Animals were then challenged with aerosolized OA (5%).

Twenty-four hours after allergen challenge the rats are anaethetized with pentobarbital (65 mg/kg) and cells are collected from the lower respiratory tract by bronchoalveolar lavage (BAL). The abdomen was opened, and the diaphragm was cut to relieve intrathoracic pressure. A tracheotomy was performed and a cannula inserted to the first bifurcation of the bronchioles. The bronchioles and alveoli were washed 10 times with 5 ml of phoaphate-buffered saline (PBS). The cells were centriguged at 200 g for 20 min and then resuspended in 1 ml of PBS. The total number of cells were counted and differentials determined with May-Grunwald/Giesma stain.

EXAMPLE 8

Inhibition by feG of a Late Phase Hypersensitivity Reaction in the Lungs

Brown Norway rats are sensitized to ovalbumin as described in EXAMPLE 7.

Twenty-one days post sensitization rats were given either an oral feG treatment (1000 ug/kg) or a saline sham treatment under light anaesthesia. Animals were then challenged with 5% OA as an aerosol. Twenty-four h following challenge, rats were anesthetized with intraperitoneal (IP) injection of urethane 1.5 mg/g body weight (Sigma), and airway hyperresponsiveness to methacholine was assessed. Briefly, animals were endotracheally intubated with polyethylene 240 tubing (Fisher Scientific, Nepean, ON Canada). Spontaneously breathing rats were placed on a heating blanket and body was maintained between 35–37 ° C. by monitoring with a rectal probe digital thermometer (Fisher scientific). The endotracheal tube was attached to a 140 ml aerosol chamber connected to a pneumotachometer (Fleish #0) connected to a Validyne (DP45±2 cm $H_2O$) differential pressure transducer and the output from the transducer was routed through Validyne amplifiers to an A/D board and computer. A water filled catheter, connected to a Transpac IV pressure transducer (Abbott Critical Care Systems), was inserted into the esophagus until a clear cardiac artifact was discernible. The Transpac IV back calibration port was connected to the aerosol chamber to obtain a transpulmonary pressure. A Transbridge 4 channel transducer amplifier (World Precision Instruments) was used with the esophageal pressure transducer and this too was routed to the A/D board and computer.

Commercially available software (RHT; infoDat Inc. Montreal, PQ, Canada) was used to obtain airways resistance (Raw) and lung elastance (E1). Throughout the experiment, the aerosol chamber was ventilated with a 2 L/min: 1 L/min ratio of air:$O_2$ except during the challenge phase of the experiment. Challenge consisted of 1 minute challenge with increasing doses of methacholine of 0.25 mg/ml to 32 mg/ml (Sigma, St. Louis Mo.) using a Hudson 880 Micromist nebulizer with an airflow of 10 L/min into the aerosol chamber. A dose response regression curve using the peak Raw value at each dose was constructed, and the methacholine value that gave a 200% increase in Raw was extrapolated from the regression line.

EXAMPLE 9

Inhibition by feG of Blood Neutrophilia Caused by an Immediate Hypersensitivity Reaction Male Hooded-Lister rats weighing 150–170 g were sensitized by intraperitoneal (i.p) injection of 10 mg of the antigen ovalbumin (OA) and 10 mg of the adjuvant aluminum hydroxide (Al(OH)$_3$) as adjuvant in saline. Control rats were injected with saline (0.9% NaCl) in the same manner. 13 days after sensitization, animals were bled via cardiac puncture to determine anti-OA IgE antibody titer via passive cutaneous anaphylaxis (PCA). Next, the animals were challenged orally with the sensitizing antigen OA (100 mg/kg). A subgroup of challenged animals was given feG (100 ig/kg) orally as a treatment. This experimental protocol received ethical approval from The University of Calgary Animal Care Committee.

Whole blood was drawn via cardiac puncture 3 h after the antigen challenge. Total leukocyte counts were determined using an Unopette microcollection system (Becton Dickinson, U.S.A) and Hylite hemocytometer (Hausser Scientific, USA). The percentage of neutrophils was determined after differential cell counts on Wright-stained blood smears.

EXAMPLE 10

Inhibition of the Platelet Activating Factor (PAF) Induced Expression of CD1b and CD16b Expression on Human Neutrophils by di- and Tripeptides Leukocytes were isolated from the blood of normal healthy volunteers. The blood (20 ml) was brought to a final volume of 50 ml with cold lysis buffer (155 mM $NH_4Cl$, 10 mM KHCO$_3$, 1 mM disodium EDTA, pH 7.4). After lysis of the erythrocytes (approximately 5 min) the cells were centrifuged at 1200 rpm for 12 min in the Beckman J6-MC using the JS 4.2 Rotor (Beckman Instruments, Mississauga, Ont.). The supernatant was discarded and the pellet was resuspended in cold lysis buffer, after 2 min cells were centrifuged again, and the leukocytes were washed with phosphate buffered saline (PBS). The solution was stored on ice until just before use at which point they were spun and resuspended at a final concentration of 10$^7$ cells per ml in Hanks balanced salt solution (HBSS) (Gibco BRL, Grand Island, N.Y.). Neutrophils were isolated to a purity of >98% in the standard manner using dextran sedimentation and Ficoll separation.

Once isolated the neutrophils were prepared to a final concentration of 5×10-6 cells/mL in phosphate buffered saline (PBS). The cells are preincubated with peptides ($10^{-8}$ to $10^{-14}$M) for 15 min prior to adding PAF (1 nM) which is added for 15 min. The cells are then centrifuged at 200×g for 6 min at 4° C., and the supernatant decanted and 50 µl of antibody, at the appropriate dilution, added to the pellet. The tube is gently vortexed. The appropriate isotype controls are prepared. The neutrophils are incubated with antibody for 30 min at 4° C. in the dark. Following this incubation 1 ml of cold PBS is added and the tubes are centrifuged at 1300 rpm for 6 min at 4° C. The supernatant is decanted off carefully and 300 µl of PBS is added to the neutrophils and cells are read with a Fluorescence Activated Cell Sorter (FACS).

The effects of the peptides on CD11b or CD16b expression were evaluated by determining the changes in mean fluorescence intensity (MFI) of cells incubated in the presence of peptide and PAF and the those incubated in presence of PAF alone, after subtracting the background (Control) MFI expressed in cells incubated with neither PAF nor a peptide. CD11b.FITC was purchased from Caltag (CedarLane) and used at 2.5 µL/5×10E5 cells. CD16a.FITC from CedarLane was used at 3 µL/5×$10^{-5}$ cells. CD16b.FITC was purchased from Immunotech (Coulter) and used at 6 µL/5×$10^{-5}$ cells.

EXAMPLE 11

Comparison of the Effects of yeG and YEG on CD11b Expression on Human Neutrophils Neutrophils were isolated according to standard protocols, as described in EXAMPLE 9. Once isolated the neutrophils were prepared to a final concentration of 5×10-6 cells/mL in phosphate buffered saline (PBS). The cells are preincubated with yeG or YEG ($10^{-8}$ to $10^{-14}$M) for 15 min prior to adding PAF (1 nM) which is added for 15 min before adding the CD11b antibody. CD11b.FITC was purchased from Caltag (CedarLane) and used at 2.5 uL/5×10E5 cells. The cells are then centrifuged at 200×g for 6 min at 4° C., and the supernatant decanted and 50 µl of antibody, at the appropriate dilution, added to the pellet. The tube is gently vortexed. The appropriate isotype controls are prepared. The neutrophils are incubated with antibody for 30 min at 4° C. in the dark. Following this incubation 1 ml of cold PBS is added and the tubes are centrifuged at 1300 rpm for 6 min at 4° C. The supernatant is decanted off carefully and 300 µl of PBS is added to the neutrophils and cells are read with a Flourescence Activated Cell Sorter (FACS).

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

REFERENCES CITED

U.S. Patent Documents

051/395 August 1998 Mathison et al 051/395

Other References

1. Befus AD, Déry R, Davison J, Mathison R. Canadian Society of Immunology (CSI) 2000 Meeting, Quebec, Canada, Mar. 17–20, 2000a.
2. Befus AD, Déry R, Davison J, Mathison R. 23rd Collegium Internationale Allergologicum (CIA) 2000 Symposiu, Haskone, Japan, May 18–23, 2000b.
3. Befus AD, Déry R, Davison J, Mathison R. Cervical sympathetic nerve trunk-submandibular gland axis: neural control of anti-inflammatory peptides that modulate air ways inflammation. Canadian Network for Neuroimmune Biology (CANIB) Symposium, Winnipeg, Manitoba, Jun. 9–12, 2000c.
4. Carrico C J, Meakins J, Marshall J C, Fry D, Maler, R V. Arch Surg 121: 196, 1985.
5. Davison J, Befus A D, Mathison R. Canadian Network for Neuroimmune Biology (CANIB) Symposium, Winnipeg, Manitoba, Jun. 9–12, 2000.
6. Déry, R, Mathison R, Davison J and Befus A D. 1999 Alberta Respiratory Disease Symposium, Banff, Alberta, Oct. 22–24, 1999.
7. Déry R, Mathison R, Davison J and Befus A D. American Thoracic Society (ATS) 2000, Toronto, Canada, May 5–10, 2000.
8. Eskandari M K, Kalff J C, Lee K K E, Billiar T R, Bauer A J. Am J Physiol 273: G727–G734, 1997.
9. Fialho de Araujo A M, Oliveira-Filho R M, Borelli P, Mathison R D, Tavares de Lima W. (manuscript submitted).
10. Hellström P M, Al-Saffar A, Ljung T, Theodorsson E: Dig. Dis. Sci. 42: 1640–1651, 1997.
11. Kosecka U, Marshall J S, Crowe S E, Bienenstock J, Perdue M H. Amer. J. Physiol. 267:G745–53, 1994.
12. Mathison R, Davison J S, Befus D. Am J Physiol 258:H1126,1990.
13. Mathison R, Befus D, Davison J S. Circ Shock 39:52, 1993.
14. Mathison R, Davison J S, Befus A D. Immunology Today 15:527, 1994.
15. Mathison R. Biomedical Reviews 4:61, 1995.
16. Mathison R D, Befus A D, Davison J S. Proc West Pharmacol Soc 40: 5–7, 1997a.
17. Mathison R D, Befus A D, Davison J S. Am J Physiol. 273: R1017–R1023, 1997b.
18. Mathison R D, Daimen T, Oliver M, Befus A D,Davison J S, Scott B. Dig Dis Sci 42: 2378–2383, 1997c.
19. Mathison R D, Davison J S, Moore G. Drug Discovery Research 42:164–171, 1997d.
20. Mathison R D, Lo, P., Davison J S, Scott B, Moore G. Peptides 19: 1037–1042, 1998.
21. Mathison R D, Sank C, Davison J S. Proc West Pharmacol Soc 42: 39–40, 1999.
22. Mathison R, Kubera M, Davison J S, Pol J Pharmacol 51:331–339, 1999a.
23. Mathison R, Oland L and Davison J S. Falk Symposium: Neurogastroenterology—From the Basics to the Clinics, Jun. 21–22, 1999b.
24. Mathison R, Oland L and Davison J S. Reduction of endotoxin-induced leukocyte activation in the rat intestine by a D-isomeric analogue of salivary gland tripeptide FEG American Gastroenterology Association, Digestive Diseases Week, San Diego, Calif., May 21–24, 2000a.
25. Mathison R, Teoh D, Woodman R, Lo P, Davison J S, Befus D. Shock 13 (Suppl): 52, 2000b.
26. Nelson D P, Samsel R W, Wood A D H, Schumacker P T. J Appl Physiol 64: 2410, 1988.
27. Nkemdirim M, Kubera M, Mathison R D. Pol. J. Pharmacol. 50: 417–424, 1998.
28. Ramaswamy K, Mathison R, Carter L, Kirk D, Green F, Davison J S, Befus A D. J Exp Med 172:1819–1830, 1990.
29. Scott R B, Tan D T M. Can. J. Physiol. Pharmacol. 74:320–30; 1996.
30. Turesin F, Mathison R, Davison J S. Shock 13 (Suppl): 52, 2000.
31. Wheeler A P, Hardie W D, Bernard, G. Am. Rev. Respir. Dis., 142:775–81, 1990.

$R_2$ is selected from the group consisting of D or L-glutamate; and aspartate;

$R_3$ is selected from the group consisting of glycine; D or L-alanine; beta-alanine; valine; leucine; isoleucine; sarcosine; and gamma-aminobutyric acid or another aliphatic amino acid; and Y is $NH_2$.

3. A peptide of the formula (II):

$$X-R_1-R_2-Y$$

wherein;

X is selected from the group consisting of H and acetyl;

$R_1$ is selected from the group consisting of D or L-phenylalanine; tyrosine; tryptophan; phenylglycine; Nor-methylphenylalanine; cyclohexylalanine; and nor-leucine;

$R_2$ is selected from the group consisting of D or L-glutamate; and aspartate; Y is $NH_2$.

What is claimed is:

1. A peptide of the formula:

$$X-R_1-R_2-R_3-Y \quad (I)$$

or $$X-R_1-R_2-Y \quad (II)$$

wherein;

X is selected from the group consisting of H and acetyl;

$R_1$ is selected from the group consisting of D or L-phenylalanine; tyrosine; tryptophan; phenylglycine; Nor-methylphenylalanine; cyclohexylalanine; and nor-leucine;

$R_2$ is selected from the group consisting of D or L-glutamate; and aspartate;

and in the case of peptide (I), $R_3$ is selected from the group consisting of glycine; D or L-alanine; beta-alanine; valine; leucine; isoleucine; sarcosine; and gamma-aminobutyric acid or another aliphatic amino acid; and Y is $NH_2$.

2. A peptide of the formula (I):

$$X-R_1-R_2-R_3-Y$$

wherein;

X is selected from the group consisting of H and acetyl;

$R_1$ is selected from the group consisting of D or L-phenylalanine; tyrosine; tryptophan; phenylglycine; Nor-methylphenylalanine; cyclohexylalanine; and nor-leucine;

4. The peptide according to claim 2 wherein X is hydrogen.

5. The peptide according to claim 2 wherein $R_1$ is D-phenylalanine.

6. The peptide according to claim 2 wherein $R_1$ is D-tyrosine.

7. The peptide according to claim 2 wherein $R_1$ is D-tryptophan.

8. The peptide according to claim 2 wherein $R_2$ is D-glutamate.

9. The peptide according to claim 2 wherein $R_3$ is glycine.

10. The peptide according to claim 3 wherein X is hydrogen.

11. The peptide according to claim 3 wherein $R_1$ is D-phenylalanine.

12. The peptide according to claim 3 wherein $R_1$ is D-tyrosine.

13. The peptide according to claim 3 wherein $R_1$ is D-tryptophan.

14. The peptide according to claim 3 wherein $R_2$ is D-glutamate.

15. A pharmaceutical composition containing a peptide according to claim 1 wherein said peptide is present in admixture with a pharmaceutically acceptable carrier.

16. The pharmaceutical composition according to claim 15 wherein the peptide is present in admixture with another therapeutically active agent.

17. A method of modulating inflammatory reactions in an animal which comprises administering to the animal a peptide according to claim 1 in an amount ranging from about 0. 1 to about 1000 µg/kg.

18. A method for the treatment of allergic disorders in an animal which comprises administering to the animal a pharmaceutical composition as claimed in claimed 15.

19. A method as claimed in claim 17 wherein the animal is a human being.

20. A method as claimed in claim 18 wherein the animal is a human being.

21. A method as claimed in claim 18, wherein said disorder is an intestinal allergy.

22. A method as claimed in claim 18, wherein said disorder is asthma.

23. A method as claimed in claim 18, wherein said disorder is rhinitis.

24. A method as claimed in claim 18, wherein said disorder is an anaphylactic reaction.

25. A method for the treatment of a toxic immunological reaction in an animal which comprises administering to the animal a pharmaceutical composition as claimed in claim 15.

26. A method as claimed in claim 25, wherein said toxic immunological reaction involves products released from or on the surface of Gram-negative bacteria, Gram-positive bacteria, fungi, viruses or parasites.

27. A method as claimed in claim 26, wherein said toxic immunological reaction involves inflammation of the respiratory system.

28. A method as claimed in claim 26, wherein said toxic immunological reaction involves inflammation of the gastrointestinal tract.

29. A method as claimed in claim 26, wherein said toxic immunological reaction involves inflammation of the heart or cardiovascular system.

30. A method as claimed in claim 26, wherein said toxic immunological reaction involves inflammation of the skin, eyes or kidneys.

31. A peptide selected from the group consisting of:

peptide #6 H-D-phe-D-glu-Gly-NH$_2$;

peptide #7 H-D-tyr-D-glu-Gly-NH$_2$;

peptide #8 H-D-trp-D-glu-Gly-NH$_2$;

peptide #9 H-D-NMef-D-glu-Gly-NH$_2$;

peptide #10 H-D-cha-D-glu-Gly-NH$_2$;

peptide #11 H-D-nle-D-asp-Gly-NH$_2$;

peptide #17 H-D-phe-D-glu-NH$_2$;

peptide #18 H-D-tyr-D-glu-NH$_2$;

peptide #19 D-trp-D-glu-NH$_2$;

peptide #20 H-D-NMef-D-glu-NH$_2$;

peptide #21 H-D-cha-D-glu-NH$_2$; and peptide #22 H-D-nle-D-asp-NH$_2$.

32. A pharmaceutical composition comprising at least one peptide selected from the group consisting of:

peptide #6 H-D-phe-D-glu-Gly-NH$_2$;

peptide #7 H-D-tyr-D-glu-Gly-NH$_2$;

peptide #8 H-D-trp-D-glu-Gly-NH$_2$;

peptide #9 H-D-NMef-D-glu-Gly-NH$_2$;

peptide #10 H-D-cha-D-glu-Gly-NH$_2$;

peptide #11 H-D-nle-D-asp-Gly-NH$_2$;

peptide #17 H-D-phe-D-glu-NH$_2$;

peptide #18 H-D-tyr-D-glu-NH$_2$;

peptide #19 D-trp-D-glu-NH$_2$;

peptide #20 H-D-NMef-D-glu-NH$_2$;

peptide #21 H-D-cha-D-glu-NH$_2$; and peptide #22 H-D-nle-D-asp-NH$_2$;

and a pharmaceutical carrier.

* * * * *

SEQUENCE LISTING

```
<160> NUMBER OF SEQ ID NOS: 1

<210> SEQ ID NO 1
<211> LENGTH: 7
<212> TYPE: PRT
<213> ORGANISM: Submandibular gland peptide-T

<400> SEQUENCE: 1

Thr Asp Ile Phe Glu Gly Gly
1               5
```